United States Patent
Qian

(10) Patent No.: US 11,014,981 B2
(45) Date of Patent: May 25, 2021

(54) METHOD FOR PREPARING NEW TYPE OF RECOMBINANT ANTI-TNF-α CHIMERIC MONOCLONAL ANTIBODY AND USE

(71) Applicant: Shanghai Biomabs Pharmaceuticals Co., Ltd., Shanghai (CN)

(72) Inventor: Weizhu Qian, Shanghai (CN)

(73) Assignee: Shanghai Biomabs Pharmaceuticals Co., Ltd., Shanghai (CN)

( * ) Notice: Subject to any disclaimer, the term of this patent is extended or adjusted under 35 U.S.C. 154(b) by 735 days.

(21) Appl. No.: 15/541,996

(22) PCT Filed: Jan. 4, 2016

(86) PCT No.: PCT/CN2016/070025
§ 371 (c)(1),
(2) Date: Oct. 30, 2017

(87) PCT Pub. No.: WO2016/110227
PCT Pub. Date: Jul. 14, 2016

(65) Prior Publication Data
US 2020/0123244 A1    Apr. 23, 2020

(30) Foreign Application Priority Data

Jan. 7, 2015  (CN) .......................... 201510004710.6

(51) Int. Cl.
| | | |
|---|---|---|
| *C07K 16/24* | (2006.01) | |
| *A61P 17/06* | (2006.01) | |
| *A61P 19/02* | (2006.01) | |
| *A61K 39/395* | (2006.01) | |
| *C12N 15/85* | (2006.01) | |
| *A61K 39/00* | (2006.01) | |
| *C12N 15/62* | (2006.01) | |
| *C12N 15/79* | (2006.01) | |
| *A61K 31/519* | (2006.01) | |

(52) U.S. Cl.
CPC .......... *C07K 16/241* (2013.01); *A61K 31/519* (2013.01); *A61K 39/3955* (2013.01); *A61P 17/06* (2018.01); *A61P 19/02* (2018.01); *C12N 15/85* (2013.01); *A61K 2039/505* (2013.01); *C07K 2317/14* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,754,853 B2 * | 7/2010 | Hellendoorn | ........ | C07K 16/241 |
| | | | | 530/326 |
| 2006/0018903 A1 | 1/2006 | Hellendoorn et al. | | |
| 2012/0077213 A1* | 3/2012 | Pla | .......................... | C07K 16/00 |
| | | | | 435/14 |
| 2014/0087392 A1 | 3/2014 | Meador, III | | |
| 2014/0161816 A1* | 6/2014 | Heavner | ................ | A61K 38/27 |
| | | | | 424/158.1 |

FOREIGN PATENT DOCUMENTS

| | | |
|---|---|---|
| JP | 2013510574 A | 3/2013 |
| JP | 2013532954 A | 8/2013 |
| WO | 2014058389 A1 | 4/2014 |
| WO | 2014134657 A1 | 9/2014 |

OTHER PUBLICATIONS

Balabashin, et al., Production of Anti TNF-a Antibodies in Eukaryotic Cells Using Different Combinations of Vectors Carrying Heavy and Light Chains, Cytotechnology, 2015, 67:761-772.
Beck, Biosimilar, Biobetter and Next Generation Therapeutic Antibodies, mAbs, 2011, 3:2, pp. 107-110.
Beck, et al., Marketing Approval of Mogamulizumab, A Triumph for Glyco-Engineering, mAbs, 2012, 4:4, pp. 419-425.
Fan, et al., Development of a Highly-Efficient Cho Cell Line Generation System with Engineered SV40E Promoter, Journal of Biotechnology, 2013, 168:652-658.
Hossler, et al., Optimal and Consistent Protein Glycosylation in Mammalian Cell Culture, Glycobiology, 2009, 19 (9):936-949.
European Patent Office, Extended European Search Report, Application No. 16734887.9, dated May 15, 2018, 8 pages.
"Pharmic Research and Phase I Clinical Study of a Novel Anti-TNFα Chimeric Monoclonal Antibody" Apr. 15, 2015, 122 pages.

\* cited by examiner

*Primary Examiner* — Gary B Nickol
*Assistant Examiner* — Jegatheesan Seharaseyon
(74) *Attorney, Agent, or Firm* — Quarles & Brady LLP

(57) ABSTRACT

Provided are a method for preparing a new type of recombinant anti-TNF-α chimeric monoclonal antibody and a use. The method comprises: designing and synthesizing the light chain and heavy chain of a CMAB008 antibody according to the preferred codon of a hamster; constructing a eukaryotic expression vector; transfecting an CHO-CR-GS –/– host cell with a GS knockout; and cultivating the cell using a serum-free culture technique; isolating and purifying; and thereby obtaining a low immunogenic CMAB008 antibody.

15 Claims, 5 Drawing Sheets

Specification includes a Sequence Listing.

METHOD FOR PREPARING NEW TYPE OF RECOMBINANT ANTI-TNF-α CHIMERIC MONOCLONAL ANTIBODY AND USE

CROSS-REFERENCE TO RELATED APPLICATIONS

This application represents the national stage entry of PCT International Application PCT/CN2016/070025 filed Jan. 4, 2016 and claims priority to Chinese Patent Application 201510004710.6 filed Jan. 7, 2015. The contents of this application are hereby incorporated by reference as if set forth in their entirety herein.

FIELD OF THE INVENTION

The present invention belongs to the field of biotechnology, and more specifically, the present invention discloses a method for preparing new type of recombinant anti-TNF-α chimeric monoclonal antibody and use.

BACKGROUND OF THE INVENTION

Rheumatoid arthritis (RA) is an autoimmune disease with the main clinical manifestations as chronic, symmetric polyarthritis, and disease relapse. The clinical manifestations include redness, swelling, pain in limbs, joints, seriously affecting the life quality of patients. If untreated, it usually can cause articular rigidity malformation within two years, leading to disabilities. Joint synovitis is the main pathological changes, and limb joints are the most vulnerable parts of the pathological invasion. The chronic inflammation is not only limited to joints and the tissues around joints, but also occurs in the heart, lungs, blood vessels and other organs or tissues.

Rheumatoid arthritis is a worldwide disease, the incidence of the disease in the United States is nearly 1%, and increases with age. The incidence rate of adults under 35 years is about 0.3%, while that for people over 65 years is more than 10%. Domestic incidence is slightly lower, about 0.3%. Considering China's large population base, the total number of patients remains high (about 4 million patients).

Rheumatoid arthritis is a common, highly destructive chronic arthritis, which is incurable, with poor long-term prognosis, greatly increasing the life cost of individual and whole economic society. If untreated, 80% of patients will gradually lose the ability to move, and reduce their average life span by 3-18 years in the United States. The annual cost of treatment per patient was $5,919 in US, or £2,600 in the UK. Current clinical used anti-rheumatic drugs are characterized with slow onset of action, limited efficacy, multiple side effects, or poor long-term prognosis.

Rheumatoid arthritis treatment can generally be divided into:

Medical treatment:

Traditional common drugs for rheumatoid arthritis therapy are: non-steroidal anti-inflammatory drugs (NSAIDs), disease modifying anti-rheumatic drugs remission (DMARDs), glucocorticoids (GCS) etc.

Non-steroidal anti-inflammatory drugs are the most common class of drugs for rheumatoid arthritis, which is characterized by rapid onset, and can significantly relieve joint pain and whole body symptoms associated with rheumatoid arthritis. They include traditional NSAIDs such as diclofenac and COX-2 inhibitors such as meloxicam, nabumetone. The deficiency of such drugs is that they only alleviate the symptoms but exhibit no significant inhibition of disease progression within synovial tissue. It should also be noted that two oral forms of NSAIDs should not be taking together to avoid increasing adverse reactions. These drugs tend to provoke strong gastrointestinal side effects. While with long-term use of new generation of COX-2 inhibitors, the chance of the occurrence of cardiovascular events increases.

Disease-modifying antirheumatic are a class of drugs allowing complete remission of rheumatoid arthritis, which are characterized by slow onset, lasting effect, can prevent or slow down the destruction of synovial membrane by rheumatoid arthritis. Usually one type of DMARDs may be used in the mild symptoms; while for patients of severe disease, DMARDs combination should be considered to control the disease. Dosage reduction or switch to single DMARD may be used for maintenance treatment once complete remission achieved. These drugs include: methotrexate, sulfasalazine pyridine arsenic, penicillamine, auranofin, azathioprine, hydroxychloroquine, leflunomide etc.

In the treatment of rheumatoid arthritis, glucocorticoid drugs are used for indications of refractory rheumatoid arthritis failed after regular treatment, or used in transitional treatment for temporarily relieving symptoms and intra-articular medication. The side effects of long-term use of hormone drugs (hypertension, osteoporosis, infections, etc.) are more difficult to treat. Such drugs include prednisone, prednisolone etc. The merits and drawbacks of long-term use of low-dose hormone therapy for rheumatoid arthritis are still inconclusive. It should not be promoted unless there is definitive evidence-based medical basis.

Drug-used medical treatment should follow the rationale of early treatment, fair use of DMARDs and individualized treatment programs. A variety of treatment programs and treatment guidelines emphasis on early diagnosis, early treatment, strengthen the treatment intensity in the meanwhile, and recommend to give DMARDs combination therapy immediately after diagnosis in order to control the disease progression as quickly as possible. However, during actual treatment the joint destruction in some patients may be still further developed, thus the therapeutic effect of traditional medicine is not very satisfactory.

Biologics:

TNF-α and interleukin-1 (IL-1) are the most critical cytokines in the pathogenesis of rheumatoid arthritis. Recent years biologics targeting TNF-α and IL-1 provide more options for the RA patients. This type of drugs directly target at specific inflammation mediators in the immune system, helping quickly control the inflammation progress, which not only significantly relieve pain, stiffness and other symptoms, but also prevent further joint damage. Such drugs which have been marketed abroad include: Infliximab (trade name "Remicade™") developed and produced by U. S. company Centocor, TNF-α receptor and antibody fusion protein (Etanercept, trade name "Enbrel™", Amgen Inc., US) and recombinant fully human anti-TNF-α monoclonal antibody (Adalimumab, trade name "Humira™", Abbott, US). Domestically marketed drugs include injectable recombinant type II TNF receptor—antibody fusion protein (trade name "Etanercept®", CITIC Guojian Pharmaceutical; trade name "QiangKe", Shanghai Celgen Biopharm), imported injectable infliximab (trade name: Remicade®) by Xian Janssen. These three types of TNF-α inhibitors can significantly reduce rheumatoid factor and anti-cyclic citrullinated peptide antibody (CCP) titers. According to the statistics the overall response rate was 50-70% for these three drugs treating RA.

In addition to the drugs above, there are a variety of biologic drugs at different stages of research, including HLA-DR4 polypeptide, IDEC-131, CII collagen peptide, HLA-DRb1 vaccine, which are all expected to become effective treatment of RA.

Immune apheresis:

For refractory rheumatoid arthritis patients, who show no significant effect through regular medical treatment and had high titers of autoantibodies in the serum, immunoadsorption therapy and lymphocyte removal can be applied for treatment. These treatments can achieve long-term disease remission only when used in combination with DMARDs. The method includes plasma exchange, immunoadsorption and lymphocyte removal, etc.

Surgical treatment:

Surgical treatment includes synovectomy, arthrodesis, osteotomy and arthroplasty, with artificial joint replacement and synovectomy usually being more common. But joint replacement applies to joints of late stage of deformity and loss of normal function. Generally it applies only to patients over age 50, since the life expectancy of artificial joint is 15 to 20 years, and the common joints are knees, hips and shoulder joints. Surgical treatment can not cure the disease, but only improve joint function and improve the patient's daily living.

Other treatments:

Other treatment methods include general treatment, herbal treatment, peripheral blood stem cell transplantation, and gene therapy etc.

General treatment refers to some therapies which treat non disease cause, such as psychotherapy, exercise therapy (recovery), immobilization, bed rest, physical therapy, diet and so on. It has a major impact on the prognosis of rheumatoid arthritis.

Botanicals including TGP glycosides or ripterygium plant preparations have been used in the treatment of rheumatoid arthritis.

Stem cell transplantation is also used for severe, refractory RA. Gene therapy, though starting late, will also become a major weapon for treatment of RA with the completion of the human genome project.

Previous studies have found that, TNF-α plays a critical role in the pathogenesis of rheumatoid arthritis. TNF-α is an important inflammatory cytokine, which plays an important role in normal immune function and the cascade of reactions causing inflammation process. In the synovial fluid of patients with rheumatoid arthritis, TNF-α and other inflammatory cytokines express abundantly. As a key inflammation factor, TNF-α's function in the inflammatory cascade and possible mechanisms during rheumatoid arthritis include: (1) Induce the synthesis of IL-1, IL-6, IL-8, TGF, GM-CSF and other inflammatory cytokines; (2) stimulate the synthesis of inflammatory mediators, such as prostaglandin E2 and leukotriene B4; (3) activate leukocytes and assist their exudation to the sites of inflammation by upregulating E-selectin, vascular cell adhesion molecules and intracellular adhesion; (4) stimulate neutrophils and fibroblasts to produce collagenase and matrix metalloproteinases. In addition, TNF-α also induces apoptosis and acute phase reaction. Therefore, blocking TNF-α synthesis and function, compared with blocking other cytokines (such as IL-1), can more fully and effectively suppress the development of rheumatoid arthritis.

TNF-α inhibitors create a new era of rheumatoid arthritis treatment. TNF-α inhibitors, especially anti-TNF-α monoclonal antibody, are currently the most effective treatment of rheumatoid arthritis, with rapid onset of action, definite efficacy. But the initial anti-TNF-α monoclonal antibody for rheumatoid arthritis treatment was prepared from murine origin. Studies have found that murine monoclonal antibody as a therapeutic agent has many flaws when used in human body: strong immunogenicity, fast in vivo elimination, short half-life, resulting in limited clinical efficacy, and strong side effects. Humanized monoclonal antibody technology partially overcomes the flaws of murine anti-TNF-α monoclonal antibody. For example, the human chimeric anti-TNF-α monoclonal antibody (Infliximab, Remicade®) was obtained using upstream genetic engineering techniques, with its variable region taken from murine TNF-α monoclonal antibody, retaining the binding specificity and affinity ($Ka=10^{10}$ M-1) to the soluble fragment and transmembrane region of tumor necrosis factor, and the constant region replaced by human IgG1 constant region, greatly extending its half-life in vivo.

Infliximab neutralizes the biological activity of TNF-α, and blocks the binding of TNF-α to its receptors by binding to the soluble and transmembrane forms of TNF-α with high affinity. Meanwhile Infliximab further kills the TNF-α expressing cells through antibody-dependent cellular cytotoxicity and complement-dependent cytotoxicity. While Infliximab does not neutralize the function of TNF-α cytokine TNF-β (also known as lymphotoxin) which shares the same receptors with TNF-α.

Remicade® is a monoclonal human-mouse chimeric antibody targeting human TNF-α, comprising a mouse variable region and a human constant regions (IgG1), binding human TNF-α specifically (affinity constant of $10^{10}M^{-1}$), with a molecular weight of 149 KDa. It's sterile, white, freeze-dried powder for intravenous infusion, with each bottle containing 100 mg of Infliximab, 500 mg of sucrose, 0.5 mg of polysorbate 80, 2.2 mg of sodium dihydrogen phosphate and 6.1 milligrams of disodium hydrogen phosphate, and no preservatives. Before use, dissolve the powder with 10 ml of sterile USP injection water, pH7.2, and then dilute with saline for infusion. Remicade was first approved by US FDA on Aug. 24, 1998, for treatment of moderate to severe active Crohn's disease or Crohn's disease with fistula. Soon after, it was approved in the EU market, and has been approved for new indications successively, including rheumatoid arthritis (RA), ankylosing spondylitis (AS), psoriatic arthritis, plaque psoriasis, ulcerative colitis and ulcerative colitis children under 6 years of age. The antibody is recombinant proteins produced by DNA recombination technology and continuous mammalian cell culture perfusion technology.

Glycosylation is highly dependent on cell expression system, subclone selection, and many other factors during cell culture, such as medium composition, culture conditions which would all affect glycosylation, thereby affecting the biological activity, efficacy, immunogenicity and pharmacokinetics of the therapeutic proteins, (Efren Pacis, Marcella Yu, Jennifer Autsen, et al. *Effects of Cell Culture Conditions on Antibody N—linked Glycosylation—What Affects High Mannose 5 Glycoform*. Biotechnology and Bioengineering, 2011; 108 (10):2348-2358; Patrick Hossler, Sarwat F Khattak, Zheng Jian. *Optimal and consistent protein glycosylation in mammalian cell culture*. Glycobiology, 2009; 19 (9), 936-949; Hodoniczky J, Zheng Y Z, James D C. *Control of recombinant monoclonal antibody effector functions by Fc N-glycan remodeling in vitro*. Biotechnol Prog, 2005; 21 (6): 1644-1652).

Among the therapeutic monoclonal antibodies currently marketed, the vast majority is produced by recombinant DNA technology, and in vitro cell culture technique (Goldenberg M M. Trastuzumab, a recombinant DNA-derived humanized monoclonal antibody, a novel agent for the treatment of metastatic breast cancer. Clin Ther, 1999; 21 (2):309-18; Mariel Donzeau, Achim Knappik. *Recombinant Monoclonal Antibodies. Methods in Molecular Biology*, 2007; 378:15-31). Because of the complexity of mammalian cell structure, function and the regulation of gene expression, there is a big difference between the expression of exogenous gene in mammalian cell and its expression in prokaryotes, therefore the components required for high expression of an exogenous gene in mammalian cells are different from those in prokaryotes cells. Expression of exogenous genes in mammalian cells includes gene transcription, mRNA translation, post-translational modifications etc. Post-translational modifications include protein glycosylation, phosphorylation, formation of protein oligomers, intramolecular or intermolecular disulfide bond formation. Post-translational modification is crucial to the protein function, for example, sometimes expression has to be carried out in mammalian cells for certain proteins having biological functions, such as membrane proteins, antibodies or enzymes having specific catalytic function. CHO cells and mouse myeloma cells (NS0, SP2/0) expression system have become standard mammalian engineering cells for current therapeutic antibodies and Fc-fusion proteins (Alain Beck, Elsa Wagner-Rousset, Marie-Claire Bussat. *Trends in Glycosylation, Glycoanalysis and Glycoengineering of Therapeutic Antibodies and Fc-Fusion Proteins. Current Pharmaceutical Biotechnology*, 2008; 9 (6): 482-501). Although the integrity of the polypeptide chain seems not change under different expression systems and culture conditions, but major changes of glycosylation type cannot be ignored.

Most patients with hypersensitivity show presence of drug-specific IgE antibodies in their serum, and these anti-IgE antibodies specifically recognize α-Gal. Further study found that mouse myeloma cells (including SP2/0) contains an extra α1,3-galactosidase transferase, which mainly mediates the transfer of galactose residues from α conformation UDP-Gal to the terminal galactose residues, thereby generating α-Gal. α-Gal is a harmful non-human disaccharide, found present in the glycans of certain mAbs, especially mAbs expressed in the murine cell (Galili U. *The alpha-Gal epitope (Gal alpha 1-3 Gal beta 1-4GlcNAc-R) in xenotransplantation. Biochimie*, 2001; 83 (7):557-563; Dor F J, Alt A, Cooper D K. *Gal alpha 1,3 Gal expression on porcine pancreatic islets, testis, spleen, and thymus. Xenotransplantation*, 2004; 11 (1): 101-106; Magnusson S, Mansson J E, Strokan V et al. *Release of pig leukocytes during pig kidney perfusion and characterization of pig lymphocyte carbohydrate xenoantigens*). In some patients there is a presence of high levels of α-Gal IgE antibodies. There will be serious hypersensitivity occurring if mAbs with glycan containing α-Gal units are used for treatment. In addition, the difference of glycosylation in murine cell lines (including SP2/0) from that of human IgG is characterized by, first, it has the protein biosynthetic machinery generating the α-Gal epitope (Larsen R D, Rajan V P, Ruff M M, 20 et al *Isolation of a cDNA encoding a murine UDP galactose: beta-D-galactosyl-1,4-N-acetyl-D-glucosaminide alpha-1, 3-galactosyltransferase: expression cloning by gene transfer Proc Natl Acad Sci USA* 86, 1989; 86 (21):8227-8231; Sheeley D M, Merrill B M, Taylor L C. *Characterization of monoclonal antibody glycosylation: comparison of expression systems and identification of terminal alpha-linked galactose. Anal Biochem*, 1997; 247(1):102-110), second, murine cell lines (including SP2/0) produce N-hydroxyethyl neuraminic acid (NGNA), but not N-acetylneuraminic acid (NANA). The difference of NGNA and NANA is NGNA has an extra oxygen atom. And, glycoproteins, if they contain NGNA residues, are considered to be closely related to the immunogenicity in humans (T. Shantha Raju. *Glycosylation Variations with Expression Systems and Their Impact on Biological Activity of Therapeutic Immunoglobulins; BioProcess International* April 2003:44-53). Some therapeutic glycoproteins which have been marketed cause serious adverse reactions in the patients because they contain NGNA residues.

Remicade has been one of the leaders in biologic antibody drugs since marketed in 1998 in the United States, belonging to the "super blockbuster" drugs with sales over 4 billion US dollars. In 2013 Remicade was ranked third among the world's best-selling drug, with sales more than 8 billion dollars. The host cell used in Remicade production is SP2/0 cells, which is a mouse myeloma cell line, known to have retrovirus particles secretion. Because Remicade was marketed much earlier, the sponsor company Centocor did not process serum-free culture technology, therefore it used cell culture media which required bovine serum to be added during the drug production. There has been over more than 100 million patients who have received this antibody treatment globally during the ten plus years of Remicade use, and it showed good efficacy and tolerability, and there were no more severe adverse effects than traditional DMARDs found. Nevertheless, this product may still post the risk of viral contamination exists since the definite presence of retrovirus in SP2/0 cells and the use of bovine serum during the production process. Furthermore, SP2/0 host cells may produce a variety of non-human glycosylation, including (NGNA, Gal-α1,3-Gal) and a higher proportion of high mannose modification during antibody post-translational modification processes, which would cause immunogenicity when used for treatment.

SUMMARY OF THE INVENTION

To overcome the problems above, reduce the risk of virus contamination and immunogenicity, the present invention provides the preparation method for a novel recombinant chimeric anti-TNF-α monoclonal antibody, to obtain a novel recombinant chimeric anti-TNF-α monoclonal antibody CMAB008. The antibody has the similar biological activity as the similar drugs that have been marketed, and the product MAB008 of the present invention has low percentage of high mannose type protein modification, no Gal-α1, 3-Gal terminal galactose connections, and no NGNA terminal sialic acid modification, which may reduce immunogenicity during use; the present invention uses no animal-derived serum-free culture medium, to reduce the risk of virus contamination.

The present invention discloses:
1. A method of producing a novel recombinant chimeric anti-TNF-α monoclonal antibody, wherein said method comprising:
   a) a novel anti-TNF-α monoclonal antibody comprises a light chain comprising the nucleotide sequence of SEQ ID NO: 1 and a heavy chain comprising the nucleotide sequence of SEQ ID NO: 2;
   b) constructing recombinant plasmid using nucleic acid fragments of a), transfecting host cells, screening high-expressing clones;
   c) optimizing cell culture conditions, culturing in large scale to produce the novel recombinant chimeric anti-TNF-α monoclonal antibody, isolating and purifying antibody.

2. The method of producing a novel recombinant chimeric anti-TNF-α monoclonal antibody as provided above, wherein the coding sequences for the light chain and heavy chain of the novel recombinant chimeric anti-TNF-α monoclonal antibody are designed and synthesized according to the codons mostly preferred by Chinese hamster.

3. A vector, comprising a nucleic acid molecule for the novel recombinant chimeric anti-TNF-α monoclonal antibody and the expression regulation sequence operability linked to the said nucleic acid molecule, wherein the vector can be any one of pDR1, pcDNA3.1(+), pcDNA3.1/ZEO (+) or pDHFR.

4. The said vector above is pcDNA3.1(+), or pcDNA3.1/ZEO (+).

5. The method of producing a novel recombinant chimeric anti-TNF-α monoclonal antibody as provided above, wherein said host cell is Eukaryotic mammalian cell CHO-CR-GS$^{-/-}$.

6. The method of producing a novel recombinant chimeric anti-TNF-α monoclonal antibody as provided above, wherein the host cell is cultured in non-animal origin serum-free condition.

7. A composition comprising the novel recombinant chimeric anti-TNF-α monoclonal antibody as provided above, and a pharmaceutically acceptable carrier.

8. Use of the said novel recombinant chimeric anti-TNF-α monoclonal antibody in manufacturing drugs for treating rheumatoid arthritis, ankylosing spondylitis, psoriatic arthritis, plaque psoriasis, etc.

9. Use of said composition in manufacturing drugs for treating rheumatoid arthritis, ankylosing spondylitis, psoriatic arthritis, plaque psoriasis, etc.

10. The use as provided by any one above, further comprising administering in combination with other drugs treating rheumatoid arthritis, ankylosing spondylitis, psoriatic arthritis, plaque psoriasis, etc.

11. A method of producing a novel recombinant chimeric anti-TNF-α monoclonal antibody, wherein said method comprising:
    a) a novel recombinant chimeric anti-TNF-α monoclonal antibody comprises a light chain comprising the amino acid sequence of SEQ ID NO: 1 and a heavy chain comprising the amino acid sequence of SEQ ID NO: 3;
    b) constructing recombinant plasmid using nucleic acid fragment of a), transfecting host cell, screening high-expressing clone;
    c) optimizing cell culture conditions, culturing in large scale to produce novel recombinant chimeric anti-TNF-α monoclonal antibody, isolating and purifying antibody.
    Wherein the pH of the said cell culture is: 6.5~7.0, preferably 6.7; the temperature of cell culture is: 34~37° C., preferably 35° C.; the osmotic pressure of cell culture is: 295 mOsm/kg~360 mOsm/kg, preferably 345 mOsm/kg.

12. A composition comprising water and recombinant chimeric anti-TNF-α monoclonal antibody; wherein the antibody comprises a light chain comprising the amino acid sequence of SEQ ID NO: 2 and a heavy chain comprising the amino acid sequence of SEQ ID NO: 4; wherein the antibody does not comprise Gal-α1,3-Gal-terminal lactose connection or NGNA terminal sialic acid modification.

13. Use of said composition in manufacturing drugs for treating rheumatoid arthritis, ankylosing spondylitis, psoriatic arthritis, plaque psoriasis, etc.

14. The use as provided by above, further comprising administering in combination with other drugs treating rheumatoid arthritis, ankylosing spondylitis, psoriatic arthritis, plaque psoriasis, etc. For example, said other drugs are non-steroidal anti-inflammatory drugs, disease modifying antirheumatic drugs, glucocorticoids etc.

15. The combination drug as described above is methotrexate.

CHO cells in the present invention are the antibody expressing cells, and the glycosylation mechanism in CHO cells is very similar to that of human IgG. Early studies suggest that CHO cells lack the biosynthetic mechanism of glycoprotein containing α-Gal epitope (Sheeley D M, Merrill B M, Taylor L C *Characterization of monoclonal antibody glycosylation: comparison of expression systems and identification of terminal alpha-linked galactose Anal Biochem,* 1997; 247 (1): 102-110 Jenkins N Parekh R B, James D C. *Getting the glycosylation right: implications for the biotechnology industry Nat Biotechnol,* 1996; 14 (8): 975-981 Spellman M W, Leonard C K, Basa L J, et al *Carbohydrate structures of recombinant soluble human CD4 expressed in Chinese hamster ovary. cells Biochemistry,* 1991; 30 (9): 2395-2406 Kagawa Y, et al *Comparative study of the asparagine-linked sugar chains of natural human interferon-beta* 1 *and recombinant human interferon-beta* 1 *produced by three different mammalian cells. J Biol Chem,* 1988; 263 (33):17508-17515), while recent studies have reported the presence of α1,3-galactosidase transferase gene in CHO cells, but this gene is not expressed or at low expression state in the clone selection process (Carlos J Bosques, Brian E Collins, James W Meador III. *Chinese hamster ovary cells can produce galactose-α-1, 3-galactose antigens on proteins. Nature Biotechnology,* 2010; 28 (11): 1153-1156), therefore, the antibodies expressed in CHO cells generally do not contain α-Gal glycan. The present invention designs and synthesizes the light and heavy chains of CMAB008 antibody according to the most preferred codons by hamsters, ligates then into eukaryotic high expression vector to obtain eukaryotic expression vector carrying the light chain and heavy chain sequences. The present invention utilizes the CRISPR/Cas technology to knockout the GS gene of CHO-K1, and obtains the cell line named CHO-CR-GS$^{-/-}$, eliminating the expression of endogenous GS, which is beneficial to the screening of high expression cell clones. CHO-CR-GS$^{-/-}$ is transfected with the expression vector containing CMAB008 gene, to screen high expression clones.

The present invention developed the universal basal medium for the CHO-CR-GS$^{-/-}$, and medium type is Chemical Defined (CD) medium, i.e. according to cell growth needs, certain percentages of amino acids, vitamins, inorganic salts, glucose and trace elements are combined to make the basal medium. The basal medium can meet the growth needs for the initial screening of engineered cells. In order to further improve the antibody yield in the engineered cells, the basal medium was subjected to further specific optimization, including adding hormones, recombinant growth factors, adjusting the amount of amino acids. After repeated optimization and comparisons, it's determined in one preferred embodiment the non-animal origin serum-free medium (CHOM-B08) and supplementary medium (CHOM-S08) suitable for large-scale culture of engineered cells expressing CMAB008 antibody. The antibody expressed in the engineered cells in an optimized medium is greater than 30 pg/cell. day, using Fed-batch culture method, and the yield of the desired antibody may be greater than 3 g/L in the culture supernatant harvested from 2 weeks culture. The glycan of CMAB008 antibodies produced by this method contains less high mannose type modification, no Gal-α1,3-Gal terminal galactose connections, NGNA terminal sialic acid modification or other non-human glycosylation. In vitro and in vivo experiments demonstrated that there is no significant difference between the biological activities of CMAB008 and Remicade, while the safety and immunogenicity of CMAB008 are significantly improved.

DESCRIPTION OF THE PREFERRED EMBODIMENTS

Embodiment 1, Construction of CMAB008 Vector

Figure 1:
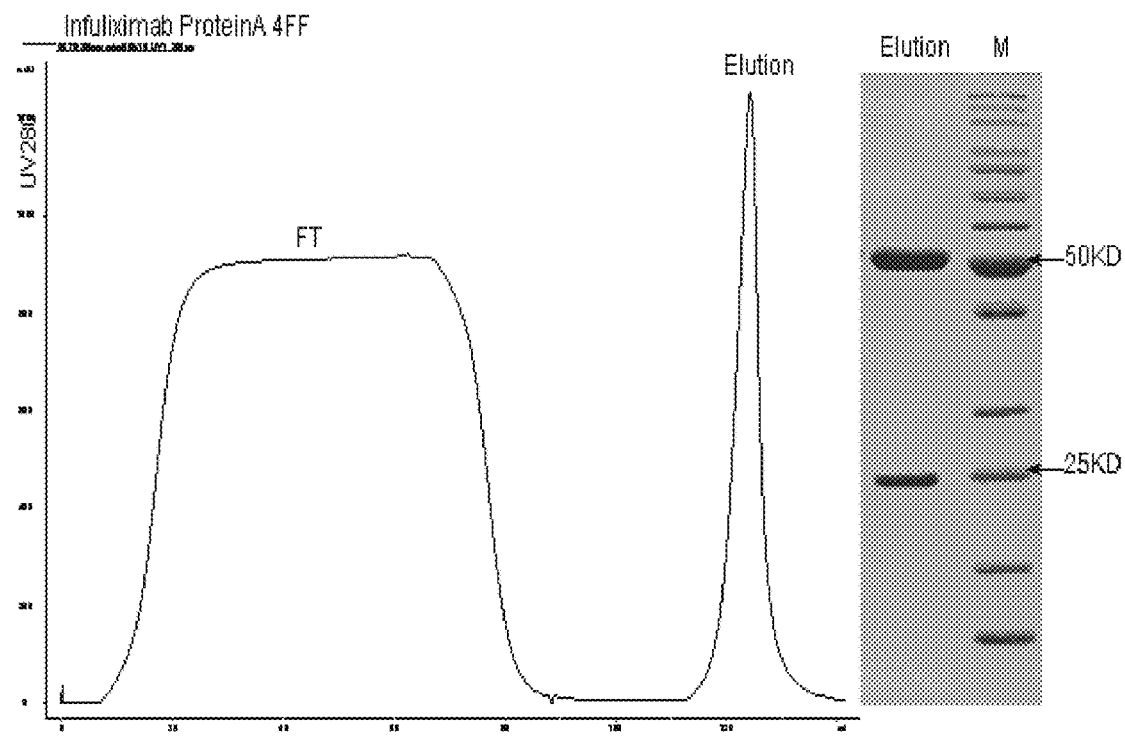
FIG. 1, The result of the isolation and purification of CMAB008 antibody.

Preferred codons of Chinese hamster were chosen for constructing efficient eukaryotic expression vector, so as to obtain more efficient expression in Chinese hamster ovary expression system. Hamsters preferred codons are shown in Table 1.

TABLE 1

Chinese hamster preferred codons

| amino acid | triplet | fraction | Frequency per thousand | number |
|---|---|---|---|---|
| G | GGC | 0.34 | 21.3 | 3268 |
|   | GGA | 0.25 | 15.8 | 2425 |
|   | GGG | 0.21 | 13.4 | 2063 |
|   | GGU | 0.20 | 12.8 | 1968 |

TABLE 1-continued

Chinese hamster preferred codons

| amino acid | triplet | fraction | Frequency per thousand | number |
|---|---|---|---|---|
| A | GCC | 0.37 | 25.9 | 3973 |
|   | GCU | 0.32 | 22.4 | 3432 |
|   | GCA | 0.23 | 16.3 | 2497 |
|   | GCG | 0.07 | 5.0 | 765 |
| V | GUG | 0.46 | 30.1 | 4628 |
|   | GUC | 0.24 | 15.7 | 2408 |
|   | GUU | 0.18 | 11.6 | 1780 |
|   | GUA | 0.12 | 7.8 | 1202 |
| L | CUG | 0.39 | 38.8 | 5955 |
|   | CUC | 0.19 | 18.4 | 2818 |
|   | UUG | 0.14 | 14.1 | 2169 |
|   | CUU | 0.13 | 13.2 | 2023 |
|   | CUA | 0.08 | 7.6 | 1174 |
|   | UUA | 0.06 | 6.4 | 978 |
| I | AUC | 0.51 | 24.8 | 3808 |
|   | AUU | 0.35 | 17.4 | 2673 |
|   | AUA | 0.14 | 6.9 | 1053 |
| F | UUC | 0.53 | 22.0 | 3381 |
|   | UUU | 0.47 | 19.6 | 3005 |
| P | CCC | 0.32 | 17.0 | 2608 |
|   | CCU | 0.31 | 16.7 | 2563 |
|   | CCA | 0.29 | 15.6 | 2388 |
|   | CCG | 0.08 | 4.3 | 657 |
| W | UGG | 1.00 | 13.1 | 2012 |
| S | UCU | 0.22 | 16.0 | 2450 |
|   | UCC | 0.22 | 16.5 | 2529 |
|   | AGC | 0.22 | 16.4 | 2521 |
|   | AGU | 0.15 | 11.4 | 1756 |
|   | UCA | 0.14 | 10.3 | 1577 |
|   | UCG | 0.05 | 3.4 | 529 |
| Y | UAC | 0.56 | 16.4 | 2519 |
|   | UAU | 0.44 | 13.1 | 2017 |
| M | AUG | 1.00 | 23.0 | 3538 |
| C | UGC | 0.53 | 10.3 | 1589 |
|   | UGU | 0.47 | 9.1 | 1397 |
| N | AAC | 0.55 | 21.2 | 3248 |
|   | AAU | 0.45 | 17.4 | 2671 |
| Q | CAG | 0.76 | 33.4 | 5122 |
|   | CAA | 0.24 | 10.3 | 1587 |
| T | ACC | 0.37 | 20.3 | 3118 |
|   | ACA | 0.29 | 15.7 | 2418 |
|   | ACU | 0.26 | 14.1 | 2172 |
|   | ACG | 0.08 | 4.5 | 685 |
| D | GAC | 0.53 | 28.1 | 4310 |
|   | GAU | 0.47 | 24.6 | 3781 |
| E | GAG | 0.59 | 41.1 | 6311 |
|   | GAA | 0.41 | 28.4 | 4355 |
| K | AAG | 0.61 | 38.4 | 5895 |
|   | AAA | 0.39 | 24.6 | 3782 |
| R | AGA | 0.19 | 10.1 | 1557 |
|   | AGG | 0.19 | 10.2 | 1570 |
|   | CGG | 0.19 | 10.1 | 1558 |
|   | CGC | 0.18 | 9.3 | 1429 |
|   | CGA | 0.14 | 7.2 | 1102 |
|   | CGU | 0.11 | 5.6 | 863 |
| H | CAC | 0.56 | 12.9 | 1980 |
|   | CAU | 0.44 | 10.2 | 1563 |
| * | UGA | 0.50 | 1.2 | 177 |
|   | UAA | 0.26 | 0.6 | 93 |
|   | UAG | 0.24 | 0.5 | 84 |

Signal peptide was selected from Chinese hamster B cell antigen receptor complex associated protein β chain. Amino acid sequence: MATMVPSSVPCHWLLFLLLLFSGSS, nucleotide sequence: ATG GCC ACC ATG GTG CCC TCT TCT GTG CCC TGC CAC TGG CTG CTG TTC CTG CTG CTG CTG TTC TCT GGC TCT TCT. This secretion signal peptide expression can better achieve antibody.

Designed and synthesized according to the most preferred codons of Chinese hamster, the CMAB009 light chain comprises the nucleotide sequence of SEQ ID NO: 1 and the amino acid sequences of SEQ ID NO: 2, the CMAB009 heavy chain comprises the nucleotide sequence SEQ ID NO:

3 and the amino acid sequence SEQ ID NO 4. The said light chain and heavy chain above were ligated into the highly efficient Eukaryotic cell expression vector to obtain the light chain and heavy chain Eukaryotic expression vector.

Embodiment 2, Selection and Engineering of the Host Cell

In the biopharmaceutical field selection of host cells needs to focus on several important aspects: glycosylation and other post-translational modifications types to avoid causing immunogenicity; host cells suitable for large-scale cultivation in bioreactors, and can grow to high density in chemically defined and animal component free (ACDF) medium; virus safety; suitable for cloning and pressure screening in the ACDF.

The majority of therapeutic monoclonal antibodies approved by FDA or EMA chose CHO cells as host cells, and a small portion chose mouse myeloma cell line, such as NS0 or SP2/0-Ag14. According to FDA reports (Erik K R, Jun T P, Kurt A B. *Division of Monoclonal Antibodies. This article is a U.S. Government work and is in the public domain of the USA,* 2011, 5(4):213□219), antibody glycans expressed in mouse myeloma cell line (NS0 and SP2/0) contain 4-6% of a (1-3) galactose, while 1% of the antibody within human circulation is against a (1-3) galactose, therefore antibodies having these glycan structures are relatively easier to cause allergic immune reactions (Alili U, Anaraki F, Thall A, et al. *One percent of 20 human circulating B lymphocytes are capable of producing the natural anti-gal antibody. Blood,* 1993, 82(8):2485-2493.). Studies have demonstrated the occurrence of hypersensitivity during the anti-EGFR chimeric antibody Cetuximab treatment is mediated by the anti-α-Galactose IgE (Chung C H, Mirakhur B, Chan E, et al. *Cetuximab-induced anaphylaxis and IgE specific for galactose-alpha-1,3-galactose. N Engl J Med,* 2008; 358 (11):1109-1117), on the other hand, murine cell line (NS0 and SP2/0) produce N-hydroxyethyl neuraminic acid (NGNA), but not N-acetyl neuraminic acid (NANA). The difference of NGNA and NANA is that NGNA has an extra oxygen atom, and, glycoproteins, if containing NGNA residues, are considered closely related to the immunogenicity in humans. Some marketed therapeutic glycoprotein cause serious adverse reactions in patients because they contain NGNA residues (O'Neil B H, Allen R, Spigel D R, et al. *High incidence of Cetuximab-related infusion reactions in Tennessee and North Carolina; association with atopic history. J Clin Oncol,* 2007; 25 (24): 3644-3648). It is because of the differences of glycosylation in CHO cells and mouse myeloma cell line (NS0 and SP2/0) mentioned above that we chose CHO cells as the expression host for CMAB008.

The most commonly used CHO cells for industrial production are the CHO-K1, CHO-DXB11 and CHO-DG44. CHO-K1 is similar to the primary CHO cells, while DXB11 and DG44 were manipulated through random mutagenesis to remove DHFR gene, so they can be used for gene amplification via metabolic defects. CHO-K1 uses GS selection system, but has a lower screening efficiency because of the endogenous GS expression in CHO-K1. The present invention chose the more widely used CHO cells as host cells which are more suitable for industrial production of therapeutic antibodies, and performed proper engineering of CHO-K1. We used CRTSPR/Cas techniques to knockout the GS gene of CHO-K1, and obtained cell line designated as CHO-CR-GS$^{-/-}$, eliminating the expression of the endogenous GS, which is therefore more beneficial for screening high expression cell clones.

Embodiment 3, Transfecting Host Cells and Screening High Expression Clones

Liposome based cotransfection of CHO-CR-GS$^{-/-}$, screening under the pressure of GS selection system were performed to obtain stable cell clones with highly efficient expression of anti-TNF-α chimeric monoclonal antibody. After several rounds of transfection and screening, cell clones were obtained with expressing amount greater than 30 pg/cell.day.

Embodiment 4, Adaptation and Optimization of Non-Animal Origin Serum-Free Culture We have developed universal basal medium for CHO-CR-GS$^{-/-}$, which is chemically defined and animal component free (ACDF) medium, i.e. the medium is made by combining certain percentages of amino acids, vitamins, inorganic salt, glucose and trace elements according to cell growth needs. This basal medium can meet the initial growth needs of the engineered cells obtained from screening. In order to control the type and extent of antibody glycosylation and further improve the desired antibody yield from the engineered cells, optimizations were carried out for the basal medium, including adding hormones, genetically engineered recombinant growth factors, and adjusting amino acids amounts. It was eventually obtained that the formulations for special medium (CHOM-B08) and special supplementary media (CHOM-S08) which are suitable for large scale non-animal origin serum-free culture of engineered cells expressing anti-TNF-α monoclonal antibody. Wide range of optimizations have been carried out for large scale culture conditions of the engineered CMAB008 expressing cell lines on culture pH, temperature, and osmolality, and it was finally established a high expression 500 L fermentation volume under fermentation conditions are: training PH, temperature and, and it was finally established the fermentation conditions for the high expression of 500 L fermentation volume: culture PH is: 6.5~7.0, preferably pH6.7; culture temperature is: 34° C.~37° C., preferably 35° C.; osmolality is: 295 mOsm/kg~360 mOsm/kg, preferably 345 mOsm/kg.

The expression yield was greater than 30 pg/cell.day for CHO cell strain expressing CMAB008 in the optimized special culture medium, with the Fed-batch culture mode, and the production of the desired antibody was over 3 g/L in the culture supernatant harvested from 2 weeks culture period.

Embodiment 5, Isolation and Purification of CMAB008 Antibody

The high expression clone obtained from the screening was cultured in expanded scale with serum-free culture medium, and the supernatant was collected, centrifuged at 9000 rpm*30 min, 4° C., to remove pellet and the cell debris; concentrated by ultrafiltration using ultrafiltration packets of 50 KD membrane from Millipore Corporation, then centrifuged at 9000 rpm*30 min, 4° C. to remove cell debris, filtered with 0.45 um membrane, used rProtein A (recombinant protein A) affinity chromatography to do preliminary purification; In-situ wash buffer is 6M GuCl, and the binding buffer for the column is 20 mM PB+150 mM NaCl pH7.0; after balancing with three to five column volumes, used three to five column volumes of elution buffer 20 mM Citric Acid (citrate buffer) pH3.0 to elute and obtain the desired protein CMAB008 of high purity, affinity chromatography and SDS-PAGE results shown in FIG. 1. The desired protein was desalted and buffer exchanged using Hitrap G25 (GE Healthcare), the column elution buffer is PBS (20 mM PB+150 mM NaCl pH7.0), in-situ washing solution is 0.5 M NaOH. All of the purification steps above were performed on ice, and the purified antibodies were concentrated with 50 KD ultrafiltration centrifuge tubes (Merck Millipore) and finally, were quantified by measuring OD 280 nm values of UV absorption. The OD280 ultraviolet absorption coefficient for CMAB008 was 1.35, and the measured OD value was divided by 1.35 to obtain the concentration (mg/ml).

Example 1, Tem of Engineering Cells

Figure 2:
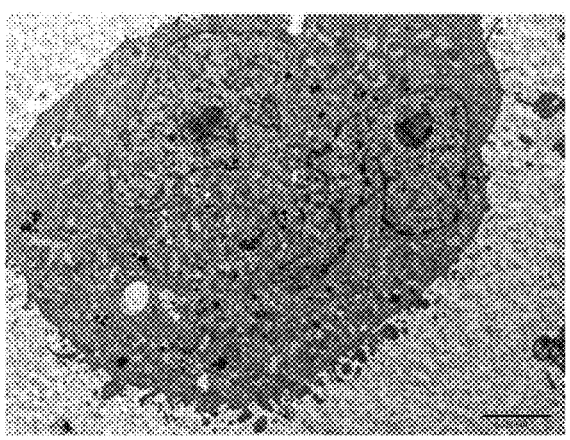
FIG. 2, Electron microscopy of the engineered CHO-CR-GS$^{-/-}$ cells, showing no viral particles.
Figure 3:
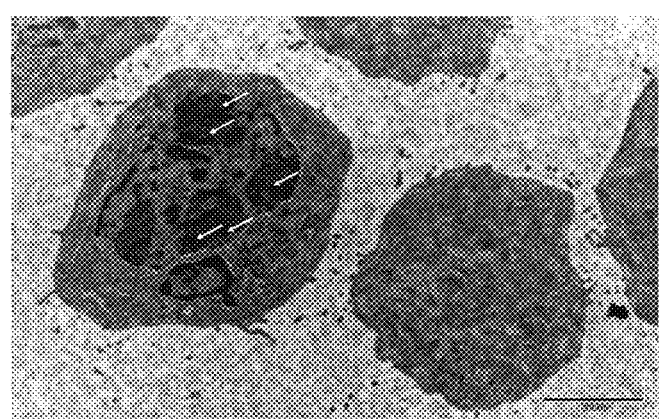
FIG. 3, Electron microscopy of SP2/0 cells, with arrow indicating viral particles.

The results showed that there are no retroviral particles in the CHO-CR-GS$^{-/-}$ engineering cells used for the antibody production (FIG. 2), while retroviral particles were clearly seen in the control, SP2/0 cells (FIG. 3). This means that the risk of Remicade, expressed in SP2/0 cells, being contaminated by virus was higher than that of CMAB008 expressed in CHO cells.

Example 2, Cmab008 Antibody Glycosylation Analysis

Figure 4:
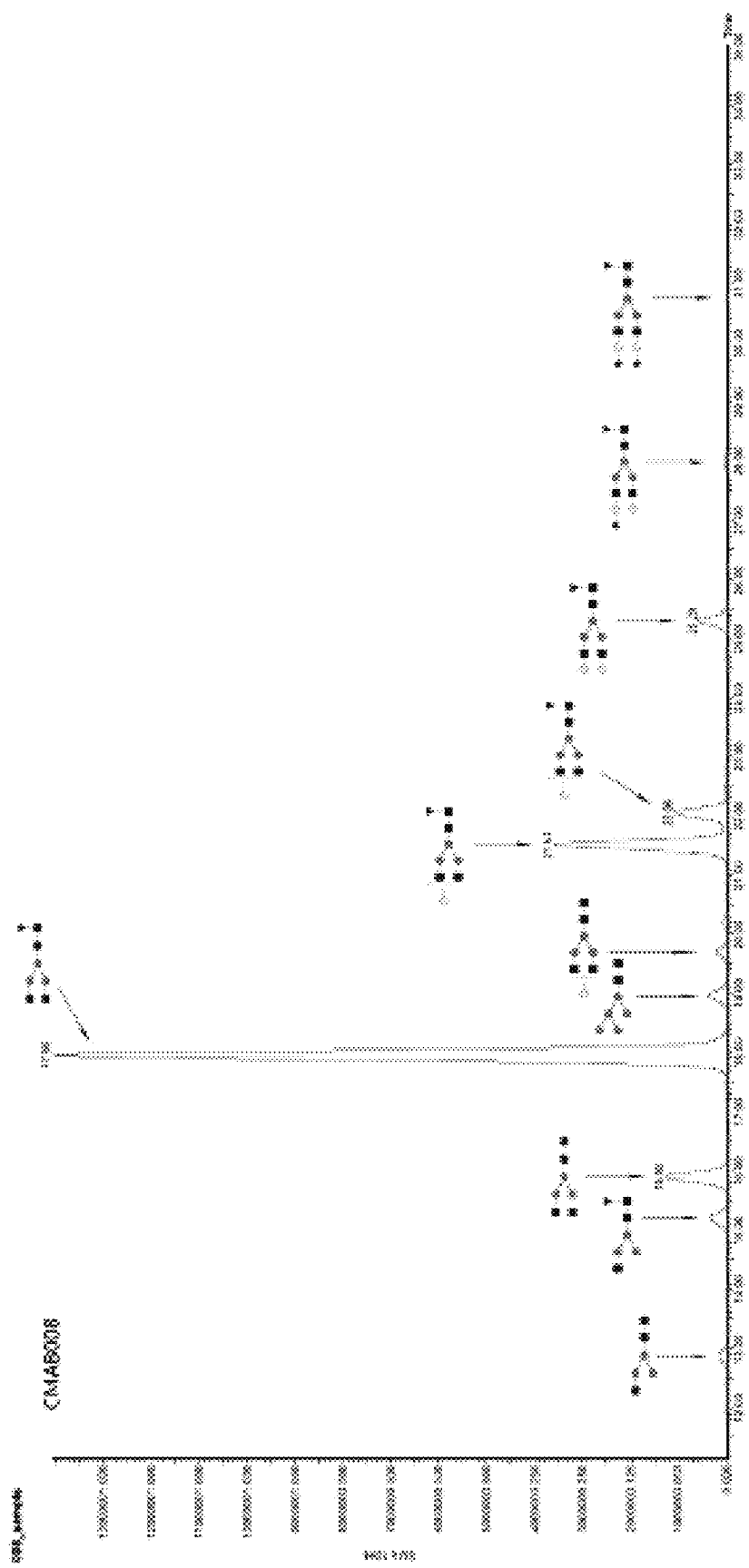
FIG. 4, Fluorescence chromatogram of 2-AB labeled CMAB008 oligosaccharides (glycan structure by mass spectrometry Mass appraisal).
Figure 5:
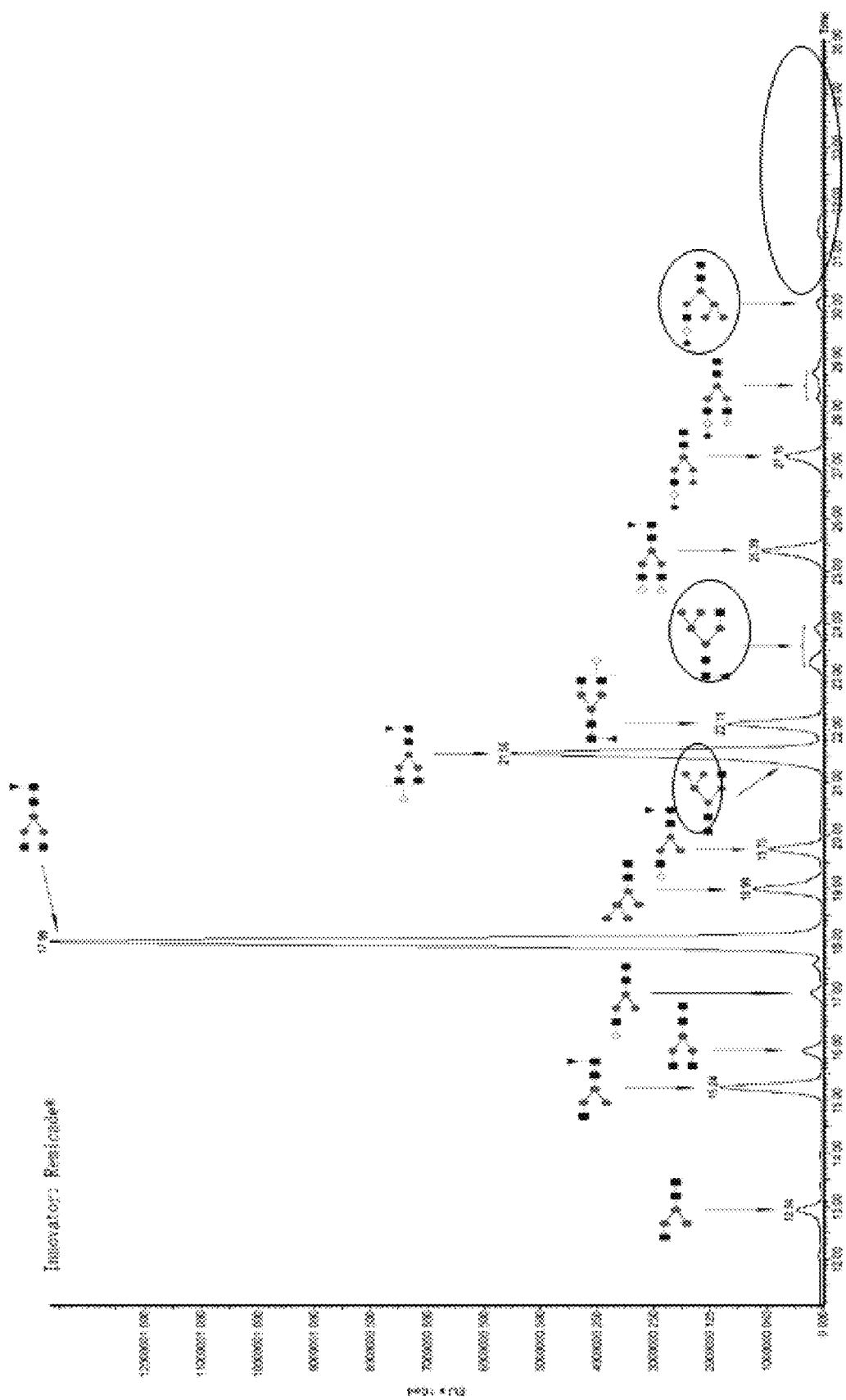
FIG. 5, Fluorescence chromatogram of 2-AB labeled Remicade oligosaccharide (glycan structure by mass spectrometry Mass appraisal). Test showed Remicade contains more types of glycans, and contains high levels of hybrid-type glycans and immunogenicity-inducing glycan type. See red circle marks, the last red circle marked glycan type is the one containing NGNA and Gal-α-Gal glycan type.

To compare the type, site, extent of the glycosylation of CMAB008 expressed in CHO and Remicade expressed in SP2/0, HPLC/MS method was used to examine the glycosylation, and the specific steps were as the following: use pH 8.0, 50 mM NH4HCO3 to dissolve antibody samples, mix with recombinant glycosidases already aliquoted, set up 100 ul reaction volume, 37° C. incubation for 24 hours. Preparation of 2-AB fluorescence labeled oligosaccharides:

Step 1 Protein removal and desalination of antibody samples after enzyme digestion: Use HILIC SPE, vacuum centrifuge and lyophilize Step 2 30% acetic acid+70% DMSO are applied to dissolve lyophilized antibody Step 3 2-AB is added to a final concentration of 50 mg/ml, sodium cyanoborohydride to 60 mg/ml, 65° C., dry bath in dark Step 4 Removing excess labeling reagent from antibody sample: Use HILIC SPE, ready to detect Using ACQUITY UPLC BEH 300 Amide 1.7 m 2.1*100 mm as the detection column, fluorescence detectors for measuring, and LC-MS mass spectrometry was used to confirm glycan types. Results were shown in FIG. 4, and FIG. 5. The red circle in FIG. 5 marks hybrid-type glycans and immunogenicity-inducing glycan type, and the last red circle marked glycan type contains NGNA and Gal-α-Gal glycan type.

According to the test results: high mannose type, its proportion in CMAB008 was very low; There was no Gal-α1,3-Gal terminal galactose connections in CMAB008; There was no NGNA terminal sialic acid modification in CMAB008.

The numbers of glycan type and structure of CMAB008 product were consistent with those of products from CHO cells, and had a great difference from those of Remicade. Remicade contained more hybrid type glycans and NGNA-containing glycans, with relative abundance over 5%, fucose glycosylated hybrid type glycan ratio reaching nearly 2%, and there was also greater than 1% glycan type having NGNA and Gal-α-Gal modifications in Remicade. These is immunogenicity risk for these non-human origin glycan types (Biotechnology and Genetic Engineering Reviews—Vol. 28, 147-176 (2012)).

Since Remicade contained higher levels of hybrid-type glycans and immunogenicity-inducing glycan, while CMAB008 does not, we speculated that it might have a better half-life and lower cell immunogenicity (clinical trials have shown that local infusion reactions of CMAB008 were much less than those reported for Remicade, see Example 7), which was closely related to the producing cells we chose and the optimization of cell culture media and culture conditions.

Example 3, Affinity Analysis

To compare the difference of binding activity for CMAB008 expressed in CHO and Remicade expressed in SP2/0, biofilm interferometry (BLI) was used to examine and compare the affinity constants of CMAB008 and Remicade with the Octet biomolecular interaction workstation (ForteBio USA). TNF-α was purchased from R&D Systems, Inc. (Catalog Number: 210-T/CF), protein sensor was preincubated in the sample diluent (0.02% Tween-20, 150 mM NaCl, 1 mg/mL BSA, 10 mM phosphate buffer, 0.05% sodium azide) for at least 5 minutes for hydration. All samples were diluted in this buffer: Remicade and CMAB008 monoclonal antibodies were diluted to 10 µg. TNF-α was diluted to the desired concentration in the sample diluent.

Experiment design: Incubating 5 minutes in sample diluent (baseline), in Remicade or CMAB008 monoclonal antibody solution 60 minutes (sample loading), 10 minutes in sample diluent (washing), 10 minutes in sample dilution (washing), 15 minutes in sample diluent (baseline), 40 minutes in TNF-α solution (binding), and buffering 60 minutes in sample diluent (separation). The results were analyzed and calculated with Fortebio analysis software with the CMAB008 affinity constant of 2.03E-10, and the Remicade affinity constant of 2.33E-10, and there was no significant difference between the two. Test results are shown in Table 2 and Table 3:

TABLE 2

Summary of CMAB008 and Remicade affinity analysis

| Samples | Lot # | Affinity Constant(M) |
|---|---|---|
| CMAB008 | 1301 | 2.03E−10 |
| Remicade | AAM05014 | 2.33E−10 |

TABLE 3

Affinity of different concentrations of CMAB008 and Remicade

| Sample | Conc. (nM) | Response | $K_D(M)$ | $K_{on}$ (1/M·s) | kon Error | Koff(1/s) | $K_{off}$ (*1/s) | Req | Full $R^2$ |
|---|---|---|---|---|---|---|---|---|---|
| CMAB008 | 20 | 2.0018 | 2.03E−10 | 9.78E+04 | 4.70E+02 | 1.98E−05 | 1.41E−06 | 2.1363 | 0.999402 |
| #1301 | 10 | 0.8318 | 2.03E−10 | 9.78E+04 | 4.70E+02 | 1.98E−05 | 1.41E−06 | 1.1185 | 0.999402 |
|  | 5 | 0.3072 | 2.03E−10 | 9.78E+04 | 4.70E+02 | 1.98E−05 | 1.41E−06 | 0.6193 | 0.999402 |
|  | 2.5 | 0.0993 | 2.03E−10 | 9.78E+04 | 4.70E+02 | 1.98E−05 | 1.41E−06 | 0.2744 | 0.999402 |
| Remicade | 40 | 2.4532 | 2.33E−10 | 9.00E+04 | 9.39E+02 | 2.10E−05 | 4.30E−06 | 2.4138 | 0.994741 |
| #AAM05014 | 20 | 1.5877 | 2.33E−10 | 9.00E+04 | 9.39E+02 | 2.10E−05 | 4.30E−06 | 1.5746 | 0.994741 |
|  | 10 | 0.6838 | 2.33E−10 | 9.00E+04 | 9.39E+02 | 2.10E−05 | 4.30E−06 | 0.8551 | 0.994741 |
|  | 5 | 0.2702 | 2.33E−10 | 9.00E+04 | 9.39E+02 | 2.10E−05 | 4.30E−06 | 0.4876 | 0.994741 |
|  | 2.5 | 0.0877 | 2.33E−10 | 9.00E+04 | 9.39E+02 | 2.10E−05 | 4.30E−06 | 0.2652 | 0.994741 |

Example 4, L929 Cell Biological Activity Analysis

To compare the differences of neutralizing TNF-α for CMAB008 expressed in CHO cells and Remicade expressed in SP2/0, TNF-α killing L929 experiment was used to examine the difference of various TNF-α antibodies in neutralizing TNF-α, the detailed methods were as follows:

(1) Obtained L929 cells of log phase, trypsin digestion, cell counting, and took approximately $2*10^6$ cells for each test (one 96 well plate), centrifuged to remove supernatant, added medium B to adjust cell density to $1.5*10^5$/ml, added to 96 well culture plate, 0.1 ml/well, and incubated overnight (18-24 h). Note that do not use the side wells of the 96 well plate, instead add sterile water in the side wells (avoiding side effects).

(2) Next day diluted 0.48 ml actinomycin D stock solution with 12 mL medium C to a final concentration of 20 μg/ml. Kept 2 ml as control (medium D), and the remaining 10 ml was added to 2.45 μl rhTNF-α stock to make a final concentration of 4.9 ng/ml (medium E).

(3) Took Remicade®, and diluted with culture medium E to 1000 ng/ml using serial dilution.

(4) Diluted CMAB008 with culture medium E to 1000 ng/ml using serial dilution.

(5) Performed serial dilution of standard or sample in 10 of 1.5 ml sterile centrifuge tube with culture medium E (i.e., each tube contains the same concentration of TNF-α or actinomycin D, but different concentration of TNF mAb after all dilution). (Please note at calculation: so the actual dilution is 2-fold dilution because solution was each added to the next well with equal volume medium).

(6) Mixed all the centrifuge tubes above thoroughly, and centrifuged at 10,000 rpm for 30 seconds to collect liquid on the bottom of the tube.

(7) Set medium E as negative, and set medium D as positive controls respectively (cells in the wells of medium D, receive no TNF killing; while cells were subjected to maximal killing in wells with medium E added).

(8) Added 0.1 ml well diluted sample or imported control, and negative or positive control media into the 96 well plates seeded with L929 cells. Every experiment was duplicated in 2 wells. Incubated in 5% CO2, 37° C. incubator.

(9) 96 well plates were incubated in the incubator for 14~16 h, add freshly prepared 20: 1 mixture of MTS/PMS solution into the wells (20 μl/well), and then incubated another 1-4 hours in the incubator before measuring value of A490-A630 with a microplate reader.

(10) Logistic regression: X-axis is standard concentration, and Y-axis is the average of light absorption value (A490-A630).

Regression equation: $Y=(A-B)/[1+(X/C)^D]+B$

According to the equation, the value of C is the median effective concentration (ED50).

Relative neutralizing activity (%)=standard ED50 (ng/mL)/test product ED50 (ng/mL)*100%

Results of three repeats of in vitro neutralizing experimental were shown in Table 4:

TABLE 4

Summary tables and in vitro test results

| Number of Experiments | EC50 (ng/ml) | | Relative affinity (%) |
|---|---|---|---|
|  | Remicade | CMAB008 |  |
| 1 | 17.32 | 16.57 | 104.53 |
| 2 | 16.19 | 17.44 | 92.83 |
| 3 | 16.91 | 16.20 | 104.38 |
| X ± S | 16.81 ± 0.57 | 16.74 ± 0.64 | 100.58 ± 6.71 |

The results from the first of these in vitro experiments are shown in Table 5:

TABLE 5

In vitro neutralization experiments Example

| | Remicade | | | CMAB008 | | |
|---|---|---|---|---|---|---|
| | Well 1 | Well 2 | Average | Well 1 | Well 2 | Average |
| ;0.98 | 0.122 | 0.139 | 0.131 | 0.118 | 0.132 | 0.125 |
| 1.95 | 0.144 | 0.137 | 0.141 | 0.137 | 0.133 | 0.135 |
| 3.91 | 0.132 | 0.186 | 0.159 | 0.128 | 0.177 | 0.152 |
| 7.81 | 0.292 | 0.264 | 0.278 | 0.277 | 0.256 | 0.267 |
| 15.63 | 0.344 | 0.406 | 0.375 | 0.334 | 0.386 | 0.360 |
| 31.25 | 0.467 | 0.521 | 0.494 | 0.484 | 0.505 | 0.495 |
| 62.50 | 0.617 | 0.561 | 0.589 | 0.598 | 0.533 | 0.566 |
| 125.00 | 0.666 | 0.637 | 0.652 | 0.590 | 0.608 | 0.599 |
| 250.00 | 0.677 | 0.637 | 0.657 | 0.657 | 0.605 | 0.631 |
| 500.00 | 0.689 | 0.663 | 0.676 | 0.698 | 0.623 | 0.661 |
| Negative | 0.134 | 0.116 | 0.125 | 0.127 | 0.113 | 0.120 |
| Positive | 0.623 | 0.658 | 0.641 | 0.602 | 0.638 | 0.620 |

Figure 6:
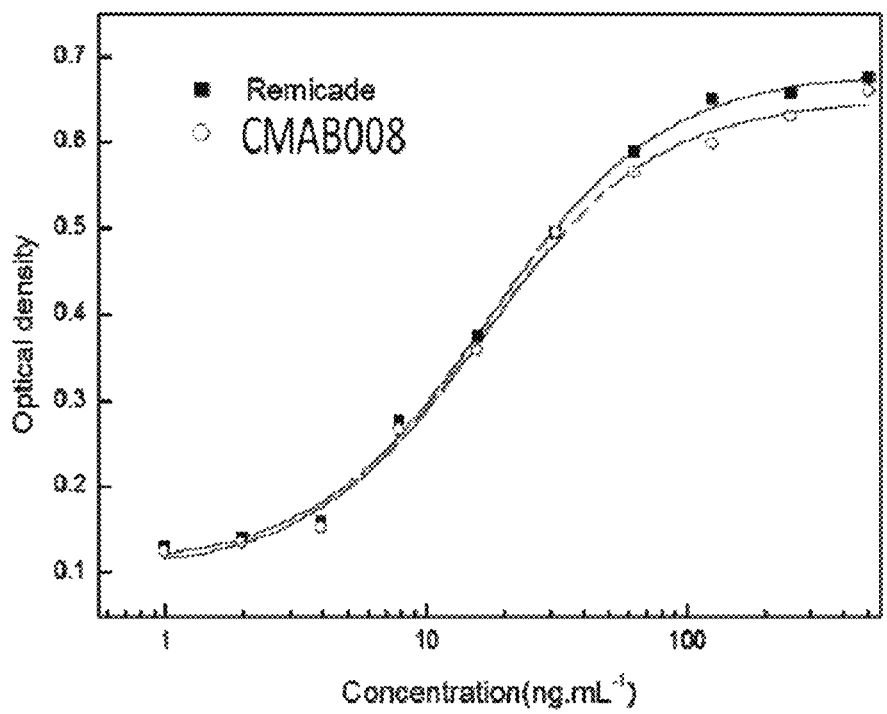
FIG. 6, Results of the comparison of CMAB008 and Remicade biological activity.
Figure 7:
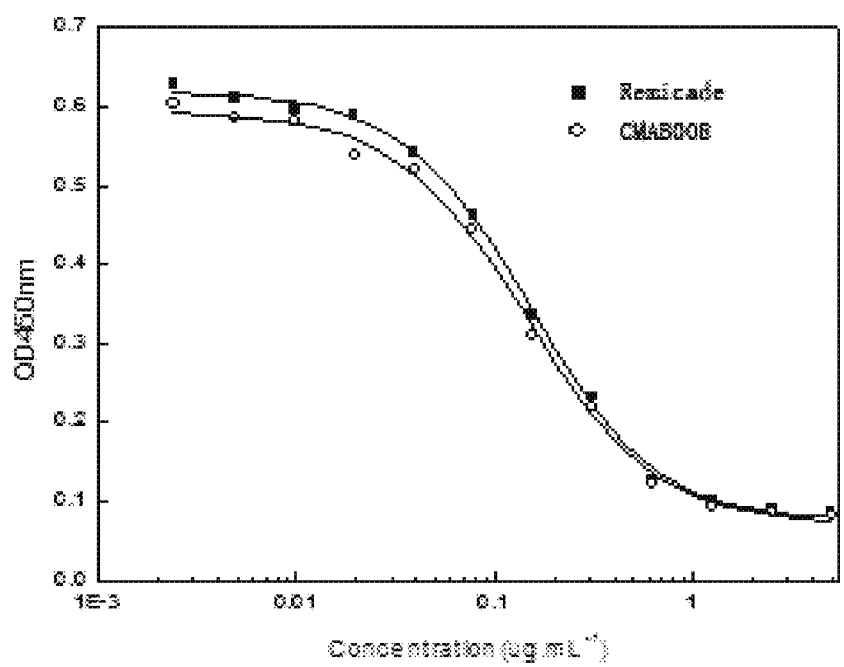
FIG. 7, ELISA test results of CMAB008 and Remicade.

The results of the regression curve were shown in FIG. 6.

Conclusion: results of in vitro neutralizing experimental showed that median effective concentrations for Remicade® and CMAB008 were 17.32 ng/ml or 16.57 ng/ml in neutralizing TNF-α or actinomycin D's killing of L929 cells, and there was no statistically significance between the two.

Example 5, Competitive ELISA Analysis of Biological Activities

Competition assays used to determine the relative affinity of CMAB008, and the affinity constants for CMAB008 was calculated and compared with those of Remicade, according to the reported affinity constants of Remicade and the calculation method. Detailed methods were as follows:

(1) TNF-α was diluted to 0.1 μg/ml with PBS, and was added to microtiter plate, 100 μl/well.

(2) Coated the plate at 37° C. for 2 hours.

(3) Discarded the liquid, washed three times with PBST, and patted dry on paper towel each time.

(4) Diluted bovine serum albumin to 3% with PBS, added into microtiter plate until the well was full.

(5) Blocking for two hours at 37° C.

(6) Discarded liquid from wells, washed three times with PBST, and patted dry on paper towel each time.

(7) Diluted HRP-labeled CMAB008 to 0.34 μg/ml with PBS, diluted Remicade to 10 μg/ml with PBS, and mixed the two in equal volume.

(8) Diluted HRP-labeled CMAB008 to 0.34 μg/ml with PBS, diluted CMAB008 to 10 μg/ml with PBS, and mixed the two in equal volume.

(9) Diluted HRP-labeled CMAB008 to 0.17 μg/ml with PBS, and used this solution to do 2× serial dilution of the Remicade and CMAB008 solutions in steps (7) and (8), respectively.

(10) Added serially diluted Remicade and CMAB008 into microtiter plates, 100 μl/well. In addition, used 0.17 μg/ml HRP-labeled CMAB008 as the strongest colour-reaction control, PBS as the weakest colour-reaction control.

(11) Incubated at 37° C. for 1 hour.

(12) Discarded the liquid, washed three times with PBST, and patted dry on paper towel each time.

(13) Mixed TMB substrate A and B in equal volume, added into microtiter plate, 100 μl/well.

(14) Incubated for 10 minutes at room temperature in the dark.

(15) Added 50 μl 0.5M sulfuric acid to each well to top reaction.

(16) Read OD450 nm with microplate reader, 630 nm reading as the reference.

Test results are summarized in Table 6:

TABLE 6

Summary of competition assay results

| Number of Experiments | EC50 (ug/ml) Remicade | CMAB008 | Relative affinity (%) |
|---|---|---|---|
| 1 | 0.149 | 0.144 | 103.5 |
| 2 | 0.127 | 0.140 | 90.7 |
| 3 | 0.142 | 0.153 | 92.8 |
| X ± S | 0.139 ± 0.011 | 0.146 ± 0.007 | 95.7 ± 6.841 |

The raw data results for the first assay are shown in Table 7:

TABLE 7

Raw data example from in vitro neutralizing experiment (optical density)

| Sample Concentration | Remicade | | | CMAB008 | | |
|---|---|---|---|---|---|---|
| | Well 1 | Well 2 | Average | Well 1 | Well 2 | Average |
| 5.0000 | 0.082 | 0.091 | 0.087 | 0.085 | 0.080 | 0.083 |
| 2.5000 | 0.087 | 0.093 | 0.090 | 0.083 | 0.087 | 0.085 |
| 1.2500 | 0.098 | 0.102 | 0.100 | 0.091 | 0.098 | 0.095 |
| 0.6250 | 0.127 | 0.130 | 0.128 | 0.113 | 0.132 | 0.122 |
| 0.3125 | 0.237 | 0.226 | 0.232 | 0.223 | 0.218 | 0.221 |

TABLE 7-continued

Raw data example from in vitro neutralizing experiment (optical density)

| Sample Concentration | Remicade | | | CMAB008 | | |
|---|---|---|---|---|---|---|
| | Well 1 | Well 2 | Average | Well 1 | Well 2 | Average |
| 0.1563 | 0.334 | 0.338 | 0.336 | 0.295 | 0.325 | 0.310 |
| 0.0781 | 0.455 | 0.469 | 0.462 | 0.417 | 0.469 | 0.443 |
| 0.0391 | 0.563 | 0.521 | 0.542 | 0.545 | 0.494 | 0.519 |
| 0.0195 | 0.588 | 0.591 | 0.590 | 0.517 | 0.563 | 0.540 |
| 0.0098 | 0.630 | 0.561 | 0.596 | 0.602 | 0.562 | 0.582 |
| 0.0049 | 0.604 | 0.617 | 0.610 | 0.597 | 0.577 | 0.587 |
| 0.0024 | 0.615 | 0.642 | 0.629 | 0.608 | 0.597 | 0.603 |
| PBS | 0.085 | 0.082 | 0.084 | 0.081 | 0.084 | 0.083 |
| HRPCMAB00 | 0.621 | 0.652 | 0.637 | 0.610 | 0.622 | 0.616 |

After calculation, the Remicade regression equation for the assay is:

$$Y=(0.61842-0.07665)/[1+(X/0.14889)^{1.38126}]+0.07665$$

CMAB008 regression equation is:

$$Y=(0.59358-0.07187)/[1+(X/0.1439)^{1.34198}]+0.07187$$

According to the literature (Ravinder N Maini and Marc Feldmann. How does infliximab work in rheumatoid arthritis Arthritis Res 2002, 4 (Suppl 2): S22-S28), Remicade affinity constant (Ka) is $10^{10}M^{-1}$. According to the calculation method reported in the literature (Berzofsky J A and Berkower I J. 1984. Fundamental Immunology. In Paul W E ed. Raven New York, pp. 595-644), we calculated the affinity constant for CMAB008 antibody tested with Remicade as the reference, and the formulation is:

$$[X]-[R]=(1/KX)-(1/KR)$$

Wherein, [X] is the EC50 of the competitive inhibition curve for sample tested, [R] is the EC50 for the reference under the same conditions; KX is the affinity constant of the sample tested, KR affinity constant for the reference.

In this experiment, the EC50 average for the samples was 0.146 μg/ml, the EC50 average for Remicade reference was 0.139 μg/ml, the difference of the two was 0.007 μg/ml, equivalent to 0.047 nM according to the monoclonal antibody molecular weight, 150 kDa; therefore, the affinity constant (Ka) for the CMAB008 tested is approximately $0.68 \times 10^{10}M^{-1}$ based on the assay above, and antigen affinities between the two can be considered essential the same.

Example 6. Study of Cmab008 and Remicade Neutralizing Tnf-α In Vivo

To compare the function of CMAB008 antibody and Remicade neutralizing human TNF-α in vivo, the two antibodies were injected into Kunming mice, to examine the effect of blocking the toxicity of rh-TNF-α.

Experimental Materials

Kunming mice (equal number of male and female), 4 to 6 weeks of age, 20±2 g/animal, purchased from the Animal Center of Second Military Medical University.

rhTNF-α is a recombinant natural type human TNF-α, purified from *E. coli* expression and purchased from R&D Systems, Inc. (catalog number: 210-T/CF).

CMAB008: provided by Shanghai Zhangjiang Biological Technology Co., Ltd., 100 mg/vial. Lot number, 20040601. Dissolved in 10 ml of sterile injectable water to a final concentration of 10 mg/ml, stored at 4° C.

Remicade (positive control): 100 mg/vial. Lot number, 101514. Dissolved in 10 ml of sterile injectable water to a final concentration of 10 mg/ml, stored at 4° C.

Negative control: 10 mmol/L phosphate saline buffer containing 5% sucrose, 0.05 mg/ml of Tween 80, pH 7.2, stored at 2~8° C. after filter sterilizing. The vehicle controls for CMAB008 and Remicade are the same.

D(+)-galactosamine: Sigma products.

Methods and Results:

Determination of the Toxic Dose of Rh-TNF-α

Because of species differences, the toxic dose of human TNF-α to mice is much higher than that of murine TNF-α. It was reported that the LD50 of human TNF-α to mice is about 4~8 mg/kg, roughly equivalent to injection of 80~160 μg per mouse[1-4]. In 1987, German scholar Lehmann first reported that the toxic effects of human TNF-α to mice can be increased by about 1,000 times by using of D(+)-galactosamine-treated mice, with LD50 of only 0.1~1.0 μg/animal[5]. Therefore, the mice toxicity mode established using D(+)-galactosamine as TNF-α sensitizers has been widely used in the research community.

120 Kunming mice (18~22 g), randomly divided into six groups (10 female and 10 male per group), were given intraperitoneal injection of different doses of rhTNF-α, 0, 0.125, 0.25, 0.5, 1.0, 2.0 μg/animal respectively, drugs dissolved in PBS, equal volume of 0.1 ml with simultaneous intraperitoneal injection of 18 mg/animal D(+)-galactosamine. Monitoring for 14 days, general activities (including eating, activity, mental, color, etc.) and survival of animals were recorded.

The results are shown in Table 8:

TABLE 8

Results of CMAB008 and Remicade neutralizing TNF-α in vivo

| Dose (ug/animal) | Logarithmic dose X | number of animals/ group n | number of animals died r | Mortality P |
|---|---|---|---|---|
| 2.0 | 0.301 | 20 | 20 | 1.00 |
| 1.0 | 0.000 | 20 | 18 | 0.90 |
| 0.5 | −0.301 | 20 | 11 | 0.55 |
| 0.25 | −0.602 | 20 | 4 | 0.20 |
| 0.125 | −0.903 | 20 | 1 | 0.05 |
| 0 | | 20 | 0 | 0.00 |
| Group intervalI = lg(2/1) = 0.301 | | | | ΣP = 2.7 |

Calculating with SPSS software, statistical analysis showed that the LD50 of rh-TNF-α for Kunming mice was 0.46 [0.30~0.60] μg/animal receiving intraperitoneal injection of 18 mg D(+)-galactosamine and rh-TNF-α, and the LD90 is 0.99 [0.77~1.83] μg/animal.

Determining In Vivo Rh-TNF-α Neutralizing Effect with Clinical Doses of CMAB008 and Remicade The clinical dosage of Remicade is 3 mg/kg, equivalent to 27 mg/kg in mice calculated according to body surface. This dose is about 500 μg per animal for mice with an average weight of 20 g (equivalent to five times of the dose predicted). We shall conduct preliminary investigation on the capability of neutralization by CMAB008 at this dose.

16 mice were randomly divided into four groups of four, equal number of male and female. Four groups of mice were each given intravenous injection of 500 μg CMAB008 or Remicade, after 72 hours, each animal was given intraperitoneal injection of 18 mg D-galactoseamines, and intraperitoneal injection of 5 μg or 10 μg rhTNF-α simultaneously.

Results: 2 days after the injection of TNF-α, 2 animals survived in CMAB008 group with injection of 10 μg rhTNF-α, and 1 animal survived in Remicade group; Whereas 4 animals survived in CMAB008 group with injection of 5 μg rhTNF-α, and 3 survived in Remicade group. Accordingly, we roughly estimate that 500 μg CMAB008 or Remicade can completely neutralize the acute toxic effects of about 5.0 μg rh-TNF-α, but only partially the acute toxicity of 10 μg rh-TNF-α. The toxic dose of rh-TNF-α after pretreatment Remicade and CMAB008 was determined.

According to the results of preliminary experiments, the following assay was designed: 240 Kunming mice were randomly divided into two large groups, each group was divided into 6 small groups, with 20 animals in each group, equal numbers of male and female, and each group was as follows:

Remicade Large Group

A. Intravenous injection of 500 μg/animal Remicade, after 72 hours, intraperitoneal injection of 0.1 ml PBS.

B. Intravenous injection of 500 μg/animal Remicade, after 72 hours, intraperitoneal injection of 20 μg/animal (0.1 ml, dissolved in PBS) rh-TNF-α, simultaneous intraperitoneal injection of 18 mg D-galactosamine.

C. Intravenous injection of 500 μg/animal Remicade, after 72 hours, intraperitoneal injection of 10 μg/animal (0.1 ml, dissolved in PBS) rh-TNF-α, simultaneous intraperitoneal injection of 18 mg D-galactosamine.

D. Intravenous injection of 500 μg/animal Remicade, after 72 hours, intraperitoneal injection of 5 μg/animal (0.1 ml, dissolved in PBS) rh-TNF-α, simultaneous intraperitoneal injection of 18 mg D-galactosamine.

E. Intravenous injection of 500 μg/animal Remicade, after 72 hours, intraperitoneal injection of 2.5 μg/animal (0.1 ml, dissolved in PBS) rh-TNF-α, simultaneous intraperitoneal injection of 18 mg D-galactosamine.

F. Intravenous injection of 500 μg/animal Remicade, after 72 hours, intraperitoneal injection of 1.25 μg/animal (0.1 ml, dissolved in PBS) rh-TNF-α, simultaneous intraperitoneal injection of 18 mg D-galactosamine.

CMAB008 Large Group

A. Intravenous injection of 500 μg/animal CMAB008, after 72 hours, intraperitoneal injection of 0.1 ml PBS.

B. Intravenous injection of 500 μg/animal CMAB008, after 72 hours, intraperitoneal injection of 20 μg/animal (0.1 ml dissolved in PBS) rh-TNF-α, simultaneous intraperitoneal injection of 18 mg D-galactosamine.

C. Intravenous injection of 500 μg/animal CMAB008, after 72 hours, intraperitoneal injection of 10 μg/animal (0.1 ml, dissolved in PBS) rh-TNF-α, simultaneous intraperitoneal injection of 18 mg D-galactosamine.

D. Intravenous injection of 500 μg/animal CMAB008, after 72 hours, intraperitoneal injection of 5 μg/animal (0.1 ml dissolved in PBS) rh-TNF-α, simultaneous intraperitoneal injection of 18 mg D-galactosamine.

E. Intravenous injection of 500 μg/animal CMAB008, after 72 hours, intraperitoneal injection of 2.5 μg/animal (0.1 ml dissolved in PBS) rh-TNF-α, simultaneous intraperitoneal injection of 18 mg D-galactosamine.

F. Intravenous injection of 500 μg/animal CMAB008, after 72 hours, intraperitoneal injection of 1.25 μg/animal (0.1 ml dissolved in PBS) rh-TNF-α, simultaneous intraperitoneal injection of 18 mg D-galactosamine.

OUTCOME MEASURES: monitoring animal survival within 72 hours after rhTNF-α injection while the animals reared under normal conditions.

The results of Remicade group are shown in Table 9:

TABLE 9

Remicade group

| Dose (ug/animal) | Logarithmic dose X | number of animals/ group n | number of animals died r | Mortality P |
|---|---|---|---|---|
| 20 | 1.301 | 20 | 19 | 0.95 |
| 10 | 1.000 | 20 | 12 | 0.60 |
| 5 | 0.699 | 20 | 5 | 0.25 |
| 2.5 | 0.398 | 20 | 3 | 0.15 |
| 1.25 | 0.097 | 20 | 1 | 0.05 |
| 0 | | 20 | 0 | 0.00 |
| Class interval I = lg(20/10) = 0.301 | | | | ΣP = 2.0 |

Figure 8:
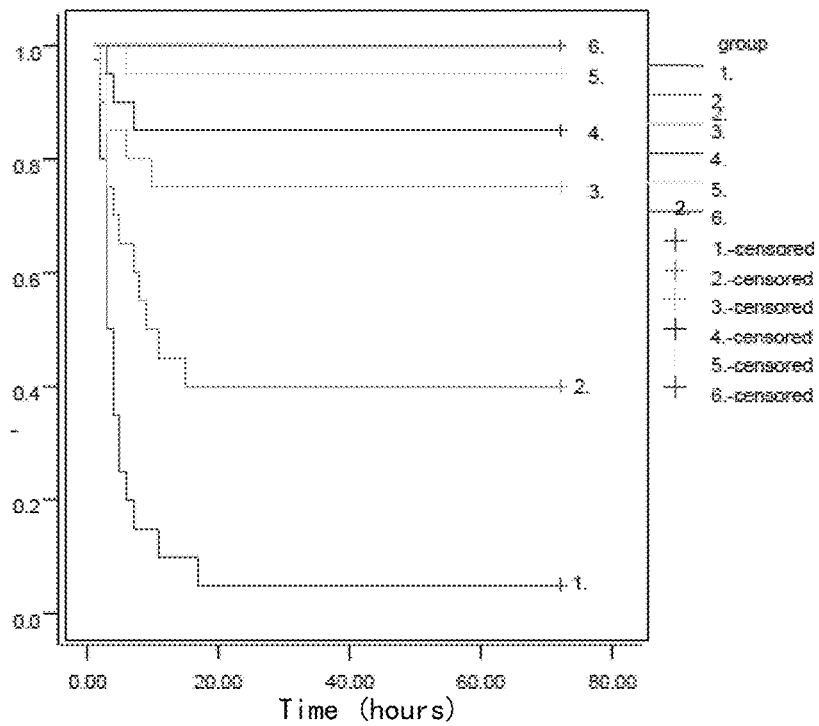
FIG. 8, Survival curves of Remicade group, injection of Remicade 500 g/animal 72 hours after intraperitoneal injection of rh-TNF- and D(+)-galactosamine 18 mg; group 1: 20 g/animal; group 2: 10 g/animal; group 3: 5 g/animal; group 4: 2.5 g/animal; group 5: 1.25 g/animal; group 6: vehicle control.

By statistical analysis, the LD50 of rh-TNF-α was 8.56 [3.85~11.30] µg/animal for Kuming mice given 500 µg/animal Remicade intravenously and intraperitoneal injection of rh-TNF-α and D(+)-galactosamine 18 mg 72 hours after. The results of survival curves are shown in FIG. 8.

The results of CMA 008 Group are shown in Table 10

TABLE 10

CMAB008 group

| Dose (ug/animal) | Logarithmic dose X | number of animals/ group n | number of animals died r | Mortality P |
|---|---|---|---|---|
| 20 | 1.301 | 20 | 18 | 0.90 |
| 10 | 1.000 | 20 | 13 | 0.65 |
| 5 | 0.699 | 20 | 4 | 0.20 |
| 2.5 | 0.398 | 20 | 2 | 0.10 |
| 1.25 | 0.097 | 20 | 1 | 0.05 |
| 0 | | 20 | 0 | 0.00 |
| Class interval I = lg(20/10) = 0.301 | | | | ΣP = 1.90 |

Figure 9:
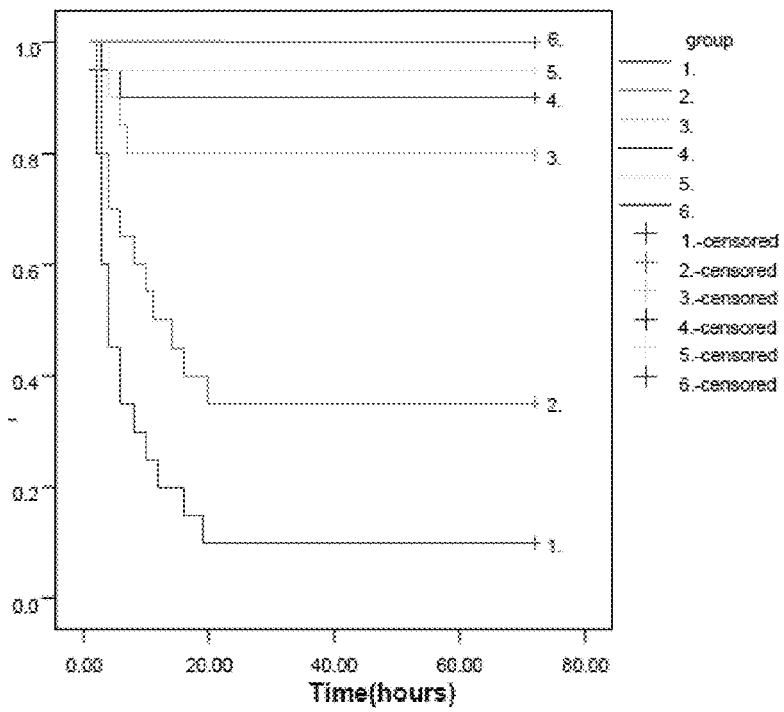
FIG. 9, Survival curves of CMAB008 group, injection of Remicade 500 g/animal 72 hours after intraperitoneal injection of rh-TNF- and D(+)-galactosamine 18 mg; group 1: 20 g/animal; group 2: 10 g/animal; group 3: 5 g/animal; group 4: 2.5 g/animal; group 5: 1.25 g/animal; group 6: vehicle control.

By statistical analysis, the LD50 of rh-TNF-α was 8.71 [5.59~11.42] µg/animal for Kuming mice given 500 µg/animal CMAB008 intravenously and intraperitoneal injection of rh-TNF-α and D(+)-galactosamine 18 mg 72 hours after. The results of survival curves are shown in FIG. 9.

These results above demonstrate that: The median lethal doses of rh-TNF-α on Kunming mice were increased from 0.46 µg/animal to 8.56 µg/animal (18.6 times) or 8.71 µg/animal (18.9 times), respectively, with intravenous injection of 500 µg/animal Remicade or CMAB008. There was no statistical difference between the 2 groups.

Experiments 7. Clinical Safety Evaluation

Phase I single dose study methods: 27 healthy subjects meeting the inclusion criteria were randomly divided into three groups, 9 subjects in each group. In low dose group, subjects were given a single intravenous infusion of 1 mg/kg CMAB008; In intermediate dose group, subjects were given a single intravenous infusion of 3 mg/kg CMAB008; In high dose group, subjects were given a single intravenous infusion of 10 mg/kg CMAB008. The infusion time is 2 hours. Blood, urine, blood tests, vital signs, electrocardiogram, chest X-ray and general symptoms was examined before the first infusion or on day 1, 28 and 56 after the intravenous infusion knot-like syndrome; Adverse events were closely observed and recorded. Single doses of 1, 3, 10 mg/kg were given in phase I, and lab results were normal among 27 subjects. Adverse reactions, from severe to mild, including dizziness, muscle aches, fever, abdominal pain, are all mild, and there were no obvious infusion-associated reactions.

There were seven cases of adverse events among a total of 27 subjects, with the incidence of adverse events adverse of 25.9%, and the results as shown in Table 11.

TABLE 11

Summary of adverse events from single dose treatments

| Group | Subject # | Symptom | Date of enrollment | Date of occurrence | Date of completion | severity | Causation | Treatment | Outcome |
|---|---|---|---|---|---|---|---|---|---|
| 10 mg/kg | 19 | dizziness | 2007 Nov. 13 | 2007 Nov. 17 | 2007 Nov. 19 | mild | May be related | rest | Improved |
| 10 mg/kg | 20 | dizziness | 2007 Nov. 13 | 2007 Nov. 17 | 2007 Nov. 19 | mild | May be related | rest | Improved |
| 10 mg/kg | 21 | dizziness | 2007 Nov. 13 | 2007 Nov. 17 | 2007 Nov. 22 | mild | May be related | rest | Improved |
| 10 mg/kg | 21 | fever | 2007 Nov. 13 | 2007 Nov. 17 | 2007 Nov. 18 | mild | May be related | Physical cooling | Improved |
| 10 mg/kg | 22 | Muscle ache | 2007 Nov. 13 | 2007 Nov. 17 | 2007 Nov. 23 | mild | May be related | rest | Improved |
| 10 mg/kg | 23 | stomach ache | 2007 Nov. 13 | 2007 Nov. 17 | 2007 Nov. 18 | mild | May be related | Observing | Improved |
| 10 mg/kg | 23 | diarrhea | 2007 Nov. 13 | 2007 Nov. 17 | 2007 Nov. 17 | mild | May be related | Observing | Improved |
| 10 mg/kg | 23 | fever | 2007 Nov. 13 | 2007 Dec. 14 | 2007 Dec. 19 | moderate | May be related | Medical treatement | Improved |
| 10 mg/kg | 23 | Elevated transaminase | 2007 Nov. 13 | 2007 Dec. 15 | 2008 Jan. 12 | moderate | May be related | Medical treatement | Improved |
| 10 mg/kg | 25 | dizziness | 2007 Nov. 13 | 2007 Nov. 17 | 2007 Nov. 18 | mild | May be related | rest | Improved |
| 10 mg/kg | 25 | Muscle ache | 2007 Nov. 13 | 2007 Nov. 18 | 2007 Nov. 23 | mild | May be related | rest | Improved |
| 10 mg/kg | 27 | right hand limp | 2007 Nov. 13 | 2007 Nov. 17 | 2007 Nov. 17 | mild | May be related | rest | Improved |

Phase I multiple-dose study methods: 9 cases of rheumatoid arthritis were enrolled and treated with the proposed therapeutic dose (3 mg/kg) for Phase II clinical trial, intravenous infusion in week 0, 2, 6, 10, 14, infusion time is two hours. Clinical observation was carried out before each treatment and at 2, 12 weeks after the last treatment. No serious adverse events occurred during the treatments and there were no any adverse reactions at injection site (redness, bruising or rash), with only one case of nausea and vomiting, which was relived after 20 minutes. The incidence rate of adverse reaction was 11.1%. Adverse events after repeated intravenous infusion of CMAB008 are shown in Table 12.

TABLE 12

Adverse events occurred after repeated CMAB008 intravenous infusion

| Number | Symptom | Severity | Causation | Evaluation of the influence of drugs | Outcome |
|---|---|---|---|---|---|
| B | Dog bites | Mild | No | No | Withdrawal from the study due to rabies vaccine, the wound healed well |
| C | Nausea, vomiting | Mild | May be related | No | Spontaneous remission after 20 minutes |
|  | Erythropenia | Mild | May be related | No | Normal blood |
|  | Hemoglobin decrease | Mild | May be related | No | Normal blood |
| D | Leukopenia | Mild | May be related | No | Normal blood |

Phase II/III clinical research methods: placebo controlled, MTX as standard treatment, randomized according to the central stratified block, double-blind, single simulation, multi-center, parallel group design superiority trial. The ratio of subject number in the study groups and the control group is 3: 1: 1, i.e. the two study groups are 330 subjects, 110 subjects, and the control group, 110 subjects. Subjects in study group A received treatment once each at week 0, 2, 6, 14, intravenous injection, 3 mg/Kg, with a total of 18 weeks treatment. Subjects in study group C received treatment once each at week 0, 2, 6, intravenous injection, 3 mg/Kg, placebo given at week 14, with a total of 18 weeks treatment. Subjects in control group B were given placebo at week 0, 2, 6, 14, intravenous infusion, with a total treatment of 18 weeks. Adverse events in each group are shown in Table 13.

During the study, the incidence rate of drug related adverse reactions are: study group A, 34.85% (115/330), control group B, 22.73% (25/110), study group C, 34.55% (38/110), and there is no statistical significance (P=0.0543) among the three groups; The adverse reaction of the highest incidence is infusion reactions: study group A, 9.70% (32/330), control group B, 1.82% (2/110), study group C, 7.27% (8/110), and there is no statistical significance (P=0.0263) among the three groups. Infusion reactions occurred during infusion or within two hours after the infusion, with symptoms including one or more the following: rash, hives, itching, numbness, faces badly bruised, swollen lips, facial edema, cough, chest tightness, shortness of breath, bronchospasm, headache, dizziness, vomiting, low blood pressure, and/or accompanied with fever, chills and other non-specific symptoms. Most infusion reactions were mild to moderate, with only 5 out of 42 subjects (11.91%) were severe; 6 out of 42 subjects (14.29%) had infusion interrupted due to infusion reactions, and 12 out of 42 patients (28.57%) withdrawn from the study due to the infusion reaction. All subjects with infusion reactions, whether receiving treatment or not, were all relieved.

The adverse reactions with incidence rate higher than 5% were: upper respiratory tract infection, study group A, 8.48% (28/330), control group B, 10.91% (12/110), and study group C, 9.09% (10/110); leukopenia, study group A, 7.58% (25/330), control group B, 3.64% (4/110), and study group C, 7.27% (8/110); abnormal liver function, study group A, 7.27% (24/330), control group B, 4.55% (5/110), and study group C, 9.09% (10/110); there is no statistical significance (P=0.0543) among the three groups.

The adverse reactions with incidence rate between 1% and 5% were: urinary system (urinary tract infection), skin and appendages (rash, urticaria, fungal dermatitis), defense system (fever, viral infection, cellular weave inflammation, lymphatic system, tuberculosis, mumps, gingivitis), systemic (fatigue, edema), gastrointestinal system (anorexia, vomiting), central and peripheral nervous system (dizziness). Except for vomiting and dizziness, the differences for all the other adverse reactions among the three groups were not statistically significant. Because the numbers for vomiting (2 cases) or dizziness (3 cases) are low, they were difficult for diagnosis due to the only single symptom, so the statistical difference may be caused by causal factors, and there are no clinical implications.

The adverse reactions with incidence rate below 1% were: red blood cells (anemia), peripheral vascular system (petechiae), heart rate and rhythm (palpitations), cardiovascular (hypertension), ocular and visual (conjunctivitis), musculoskeletal system (avascular necrosis), other (menstruation), and there was no statistical significance between the three groups.

The vast majority of adverse reactions were mild to moderate, with symptomatic remission after treatment, and no need of interruption. Severe adverse reactions totaled 7/178 patients (3.93%), with all symptoma remission after treatment: 5 subjects of infusion reactions (4 withdrawals), 1 subject of dizziness (withdrawal), 1 subject of urinary tract infection (continue treatment without withdrawal).

In the multi-center trial of Remicade's application for registration in China, the incidence rate for adverse events was 65.5% (Hou Yong Infliximab treatment of rheumatoid arthritis parallel randomized double-blind multi-center clinical trial, "Chinese Journal of Rheumatology" 2006 11 period). The incidence rate for CMAB008 adverse reaction is much lower than that of Remicade.

TABLE 13

Classification and comparison of the adverse reactions among the three groups

| | Group A | | | Group B | | | Group C | | | Incidence | |
|---|---|---|---|---|---|---|---|---|---|---|---|
| | Occurrence | Cases | Incidence (%) | Occurrence | Cases | Incidence (%) | Occurrence | Cases | Incidence (%) | Statistics | P value |
| Leukocytes and reticuloendothelial system | 33 | 26 | 7.88 | 5 | 5 | 4.55 | 8 | 8 | 7.27 | 1.40 | 0.4976 |
| Leukopenia | 31 | 25 | 7.58 | 4 | 4 | 3.64 | 8 | 8 | 7.27 | 2.10 | 0.3496 |
| Leukopenia, Neutropenia | 0 | 0 | 0.00 | 1 | 1 | 0.91 | 0 | 0 | 0.00 | 4.00 | 0.1353 |
| Thrombocytopenia | 1 | 1 | 0.30 | 0 | 0 | 0.00 | 0 | 0 | 0.00 | 0.67 | 0.7165 |
| Thrombocytopenia, Leukopenia | 1 | 1 | 0.30 | 0 | 0 | 0.00 | 0 | 0 | 0.00 | 0.67 | 0.7165 |
| Hepatobiliary system | 25 | 24 | 7.27 | 5 | 5 | 4.55 | 10 | 10 | 9.09 | 1.76 | 0.4141 |
| Abnormal liver function | 25 | 24 | 7.27 | 5 | 5 | 4.55 | 10 | 10 | 9.09 | 1.76 | 0.4141 |
| RBC | 0 | 0 | 0.00 | 0 | 0 | 0.00 | 1 | 1 | 0.91 | 4.00 | 0.1353 |
| Anemia | 0 | 0 | 0.00 | 0 | 0 | 0.00 | 1 | 1 | 0.91 | 4.00 | 0.1353 |
| Respiratory system | 42 | 35 | 10.61 | 17 | 15 | 13.64 | 16 | 13 | 11.82 | 0.76 | 0.6827 |
| cough | 2 | 2 | 0.61 | 0 | 0 | 0.00 | 1 | 1 | 0.91 | 0.89 | 0.6401 |
| Upper respiratory tract infection | 34 | 28 | 8.48 | 14 | 12 | 10.91 | 13 | 10 | 9.09 | 0.59 | 0.7462 |
| Lower respiratory infections (including pneumonia) | 3 | 3 | 0.91 | 3 | 3 | 2.73 | 2 | 2 | 1.82 | 2.03 | 0.3632 |
| pharyngitis | 3 | 3 | 0.91 | 0 | 0 | 0.00 | 0 | 0 | 0.00 | 2.01 | 0.3665 |
| Defense System | 5 | 5 | 1.52 | 2 | 2 | 1.82 | 3 | 3 | 2.73 | 0.68 | 0.7126 |
| Viral infection | 0 | 0 | 0.00 | 0 | 0 | 0.00 | 1 | 1 | 0.91 | 4.00 | 0.1353 |
| Low Fever | 1 | 1 | 0.30 | 1 | 1 | 0.91 | 0 | 0 | 0.00 | 1.34 | 0.5128 |
| Fever | 0 | 0 | 0.00 | 1 | 1 | 0.91 | 1 | 1 | 0.91 | 3.01 | 0.2225 |
| cellulitis | 0 | 0 | 0.00 | 0 | 0 | 0.00 | 1 | 1 | 0.91 | 4.00 | 0.1353 |
| Tuberculosis | 1 | 1 | 0.30 | 0 | 0 | 0.00 | 0 | 0 | 0.00 | 0.67 | 0.7165 |
| Lymph node tuberculosis | 1 | 1 | 0.30 | 0 | 0 | 0.00 | 0 | 0 | 0.00 | 0.67 | 0.7165 |
| Mumps | 1 | 1 | 0.30 | 0 | 0 | 0.00 | 0 | 0 | 0.00 | 0.67 | 0.7165 |
| Gingivitis | 1 | 1 | 0.30 | 0 | 0 | 0.00 | 0 | 0 | 0.00 | 0.67 | 0.7165 |
| Musculoskeletal System | 0 | 0 | 0.00 | 0 | 0 | 0.00 | 1 | 1 | 0.91 | 4.00 | 0.1353 |
| Avascular necrosis | 0 | 0 | 0.00 | 0 | 0 | 0.00 | 1 | 1 | 0.91 | 4.00 | 0.1353 |
| Urinary System | 11 | 9 | 2.73 | 1 | 1 | 0.91 | 1 | 1 | 0.91 | 2.22 | 0.3292 |
| Urinary tract infections | 11 | 9 | 2.73 | 1 | 1 | 0.91 | 1 | 1 | 0.91 | 2.22 | 0.3292 |
| Skin and appendages | 9 | 9 | 2.73 | 0 | 0 | 0.00 | 0 | 0 | 0.00 | 6.09 | 0.0476 |
| rash | 6 | 6 | 1.82 | 0 | 0 | 0.00 | 0 | 0 | 0.00 | 4.04 | 0.1329 |
| Rash, urticaria | 1 | 1 | 0.30 | 0 | 0 | 0.00 | 0 | 0 | 0.00 | 0.67 | 0.7165 |
| Fungal dermatitis | 1 | 1 | 0.30 | 0 | 0 | 0.00 | 0 | 0 | 0.00 | 0.67 | 0.7165 |
| Hives | 1 | 1 | 0.30 | 0 | 0 | 0.00 | 0 | 0 | 0.00 | 0.67 | 0.7165 |
| Systemic | 4 | 4 | 1.21 | 2 | 2 | 1.82 | 1 | 1 | 0.91 | 0.39 | 0.8248 |
| Weakness | 3 | 3 | 0.91 | 2 | 2 | 1.82 | 1 | 1 | 0.91 | 0.67 | 0.7143 |
| Edema | 1 | 1 | 0.30 | 0 | 0 | 0.00 | 0 | 0 | 0.00 | 0.67 | 0.7165 |
| Infusion reactions | 39 | 32 | 9.70 | 2 | 2 | 1.82 | 9 | 8 | 7.27 | 7.27 | 0.0263 |
| Infusion reactions | 17 | 13 | 3.94 | 2 | 2 | 1.82 | 3 | 3 | 2.73 | 1.30 | 0.5222 |
| Low fever | 2 | 2 | 0.61 | 0 | 0 | 0.00 | 0 | 0 | 0.00 | 1.34 | 0.5128 |
| Allergy, swollen faces, lips | 0 | 0 | 0.00 | 0 | 0 | 0.00 | 1 | 1 | 0.91 | 4.00 | 0.1353 |
| Anaphylactic shock | 2 | 2 | 0.61 | 0 | 0 | 0.00 | 0 | 0 | 0.00 | 1.34 | 0.5128 |
| Chills, fever | 1 | 1 | 0.30 | 0 | 0 | 0.00 | 0 | 0 | 0.00 | 0.67 | 0.7165 |
| Cough, chest tightness, rash | 1 | 1 | 0.30 | 0 | 0 | 0.00 | 0 | 0 | 0.00 | 0.67 | 0.7165 |
| Rash, urticaria | 1 | 1 | 0.30 | 0 | 0 | 0.00 | 0 | 0 | 0.00 | 0.67 | 0.7165 |
| Rash, itching | 6 | 5 | 1.52 | 0 | 0 | 0.00 | 1 | 1 | 0.91 | 1.79 | 0.4078 |
| Chest tightness, shortness of breath, bronchospasm | 1 | 1 | 0.30 | 0 | 0 | 0.00 | 0 | 0 | 0.00 | 0.67 | 0.7165 |
| Chest tightness, headache, dizziness | 0 | 0 | 0.00 | 0 | 0 | 0.00 | 1 | 1 | 0.91 | 4.00 | 0.1353 |
| Chest discomfort | 1 | 1 | 0.30 | 0 | 0 | 0.00 | 0 | 0 | 0.00 | 0.67 | 0.7165 |
| Hives | 4 | 3 | 0.91 | 0 | 0 | 0.00 | 1 | 1 | 0.91 | 1.01 | 0.6049 |
| Urticaria, facial edema | 0 | 0 | 0.00 | 0 | 0 | 0.00 | 1 | 1 | 0.91 | 4.00 | 0.1353 |
| Hives, vomiting | 1 | 1 | 0.30 | 0 | 0 | 0.00 | 0 | 0 | 0.00 | 0.67 | 0.7165 |
| Itching | 1 | 1 | 0.30 | 0 | 0 | 0.00 | 0 | 0 | 0.00 | 0.67 | 0.7165 |
| Itching, numbness | 1 | 1 | 0.30 | 0 | 0 | 0.00 | 0 | 0 | 0.00 | 0.67 | 0.7165 |
| Allergy, swollen faces | 0 | 0 | 0.00 | 0 | 0 | 0.00 | 1 | 1 | 0.91 | 4.00 | 0.1353 |
| Peripheral vascular | 1 | 1 | 0.30 | 0 | 0 | 0.00 | 0 | 0 | 0.00 | 0.67 | 0.7165 |
| Petechiae | 1 | 1 | 0.30 | 0 | 0 | 0.00 | 0 | 0 | 0.00 | 0.67 | 0.7165 |
| Gastrointestinal system | 2 | 2 | 0.61 | 0 | 0 | 0.00 | 2 | 2 | 1.82 | 2.68 | 0.2617 |
| Anorexia | 2 | 2 | 0.61 | 0 | 0 | 0.00 | 0 | 0 | 0.00 | 1.34 | 0.5128 |

TABLE 13-continued

Classification and comparison of the adverse reactions among the three groups

| | Group A | | | Group B | | | Group C | | | Incidence | |
|---|---|---|---|---|---|---|---|---|---|---|---|
| | Occurrence | Cases | Incidence (%) | Occurrence | Cases | Incidence (%) | Occurrence | Cases | Incidence (%) | Statistics | P value |
| Vomit | 0 | 0 | 0.00 | 0 | 0 | 0.00 | 2 | 2 | 1.82 | 8.01 | 0.0182 |
| Heart rate and rhythm | 1 | 1 | 0.30 | 0 | 0 | 0.00 | 0 | 0 | 0.00 | 0.67 | 0.7165 |
| Palpitations | 1 | 1 | 0.30 | 0 | 0 | 0.00 | 0 | 0 | 0.00 | 0.67 | 0.7165 |
| Cardiovascular | 0 | 0 | 0.00 | 0 | 0 | 0.00 | 1 | 1 | 0.91 | 4.00 | 0.1353 |
| hypertension | 0 | 0 | 0.00 | 0 | 0 | 0.00 | 1 | 1 | 0.91 | 4.00 | 0.1353 |
| Eye and Vision | 0 | 0 | 0.00 | 0 | 0 | 0.00 | 1 | 1 | 0.91 | 4.00 | 0.1353 |
| Conjunctivitis | 0 | 0 | 0.00 | 0 | 0 | 0.00 | 1 | 1 | 0.91 | 4.00 | 0.1353 |
| Central and peripheral nervous system | 0 | 0 | 0.00 | 0 | 0 | 0.00 | 3 | 3 | 2.73 | 12.04 | 0.0024 |
| dizziness | 0 | 0 | 0.00 | 0 | 0 | 0.00 | 3 | 3 | 2.73 | 12.04 | 0.0024 |
| other | 0 | 0 | 0.00 | 0 | 0 | 0.00 | 1 | 1 | 0.91 | 4.00 | 0.1353 |
| Menstruation | 0 | 0 | 0.00 | 0 | 0 | 0.00 | 1 | 1 | 0.91 | 4.00 | 0.1353 |

CMH test was used for the comparison of the incidence among the three groups, and the statistic would be the chi-square value of CMH, if the CMH test was used.

Example 8. Immunogenicity Test (1) single-dose treatment:

Methods: 27 healthy subjects meeting the inclusion criteria were randomly divided into three groups, 9 in each group. Subjects in low dose group received a single intravenous infusion of CMAB008 at 1 mg/kg; Subjects in intermediate dose group received intravenous infusion of CMAB008 at 3 mg/kg; Subjects in high dose group received intravenous infusion of CMAB008 at 10 mg/kg. The infusion time was 2 hours.

Serum anti-CMAB008 antibody (ADA) was examined after the subjects receiving CMAB008, and the serum were collected before the treatment, or on day 14, 28, 56 after treatment;

Serum ADA test were as follows:

Experimental procedures:

1) Diluted CMAB008 antibody to 0.5 μg/ml with phosphate buffered saline (PBS), added to microtiter plates (NUNC), 100 μl/well, 2) Incubated for 2 hours at 37 □ incubator or overnight at 4 □;

3) Discarded liquid in the wells, patted dry on paper towel, washed with PBS containing 0.1% Tween-20 for 3 times, patted dry on paper towel each time;

4) 3% bovine serum albumin (Shanghai Biological Engineering Co., Ltd.) (diluted in PBS) was added to microtiter plates wells until full (approximately 350 μl/well), 2 hours in 37 □ incubator or overnight at 4 □;

5) Discarded liquid in the wells, patted dry on paper towel, washed with PBS containing 0.1% Tween-20 for 3 times, patted dry on paper towel each time;

6) Diluted rabbit anti-CMAB008 polyclonal antibody (homemade by this lab, rabbits immunized with CMAB008, antiserum applied to CMAB008 affinity chromatography and purified to obtain elution peak) with PBS to 10 μg/ml, diluted positive control, negative control (pooled sera of healthy volunteers, 10-fold dilution), blank (PBS) and samples (10-fold dilution) were added to microtiter plate, 100 μl/well, experiment replicated, 2 hours at 37 □ incubator;

7) Discarded liquid in the wells, patted dry on paper towel, washed with PBS containing 0.1% Tween-20 for 3 times, patted dry on paper towel each time;

8) Diluted HRP-labeled CMAB008 (homemade by this lab, CMAB008 labeled with HRP kit from Pierce company and purified by gel filtration chromatography) 1: 500 (PBS), added to microtiter plate, 100 μl/well, 45 minutes at 37 □ incubator;

9) Discarded liquid in the wells, patted dry on paper towel, washed with PBS containing 0.1% Tween-20 for 3 times, patted dry on paper towel each time; Chemiluminescent substrates A and B (Jingmei Biological Engineering Co.) were mixed at equal volume, added to microtiter plates, 100 μl/well, incubated the reaction for 5-20 minutes at room temperature in dark (determine the time of reaction according to the color reaction);

10) Added termination reagent to microtiter plates, 50 μl/well, mixed quickly; read OD450 nm with microplate reader, 630 nm as reference wavelength.

Result evaluation:

Each plate should be set with two blank controls, two negative controls, three positive controls.

OD value of blank should be ≤0.10.

After subtracting the blank OD value, both 2 negative controls should be 0≤OD value≤0.15.

After subtracting the blank OD value, at least 2 out the three positive controls should be 0.6≤ODvalue≤2.0.

Two or more positive controls OD value may not differ by more than 30%, otherwise they should be re-tested.

The difference between positive control OD average and negative control OD average should not be less than 0.50.

C.O.=2.1*(negative control OD−blank OD)

If (sample OD−blank OD)/C.O.≥1, the sample is determined to be positive.

Serum ADA in 2 out of 9 subjects in group of 1 mg/kg (#7, #8) was tested positive, detailed results are shown in Table 14:

TABLE 14

| Serum ADA test results in group receiving single dose of 1 mg/kg | | | | | | | | | |
|---|---|---|---|---|---|---|---|---|---|
| sampling time | #1 | #2 | #3 | #4 | #5 | #6 | #7 | #8 | #9 |
| Before treatment | − | − | − | − | − | − | − | − | − |
| 2 weeks after treatment | − | − | − | − | − | − | − | − | − |
| 4 weeks after treatment | − | − | − | − | − | − | + | + | − |
| 4 weeks after treatment | − | − | − | − | − | − | − | − | − |

Further test was carried out for neutralizing antibody in ADA-positive samples, detailed methods and screening criteria are as follows:

Method:
1) Obtain L929 cells of log phase, adjust cell density to $1.5 \times 10^5$/mL with cell culture medium, add to 96 well culture plate, 0.1 mL/well, and incubate overnight (18-24 h).
2) Dilute actinomycin D with culture medium to a final concentration of 20 μg/mL the next day, add TNF-α to a concentration of 20 ng/mL, CMAB008 antibody to 200 ng/ml (diluent, keep some as blank control).
3) Dilute negative control serum 100 folds with diluent (pooled serum of healthy volunteers), as the negative control.
4) Dilute positive control with diluent to 1 μg/ml.
5) Dilute samples 100-fold with diluent.
6) Add the samples, negative, positive and blank controls above to 96-well plates, 0.1 mL/well, experiment replicate, and incubate overnight (18-24 h).
7) Endpoint test: after 14~16 h in the incubator, 96 well plates were added with freshly prepared 20:1 mixture of MTS/PMS solution, 20 μL/well, incubate for 1-4 hours in the incubator (96 well plate without cover lid), read A490-A630 value with a microplate reader.

Result evaluation:
Each microplate should be set with two blank controls, two negative controls, and three positive controls.
Blank OD value should be ≥0.80.
Both negative control OD value should be ≥0.80.
At least two of the three positive controls should be: OD value≤0.40.
No more than two or more positive control OD values may differ by more than 30%, re-test otherwise.
The difference between positive control OD average and negative control OD average should not be less than 0.40.
C.O.=0.5* negative control OD
If sample OD/C.O.<1, it is determined as positive.

Neutralizing antibody tests were negative in the sera of #7, #8 subjects, the detailed results are shown in Table 15. Plasma CMAB008 drug concentrations were analyzed in the sera of #7, #8 subjects, and there was no significant difference found in serum drug concentrations between these 2 and other subjects.

TABLE 15

Serum neutralizing antibody detection in the sera of 1 mg/kg single dose group

| sampling time | #7 | #8 |
|---|---|---|
| Before treatment | — | — |
| 4 weeks after treatment | — | — |

Serum anti-CMAB008 antibody test in subjects of 3 mg/kg dose group or 10 mg/kg dose groups subjects were both negative. Results are shown in table 16 and table 17:

TABLE 16

Serum ADA test results in 3 mg/kg single dose group

| Sampling time | #1 | #2 | #3 | #4 | #5 | #6 | #7 | #8 | #9 |
|---|---|---|---|---|---|---|---|---|---|
| Before treatment | – | – | – | – | – | – | – | – | – |
| 2 weeks after treatment | – | – | – | – | – | – | – | – | – |
| 4 weeks after treatment | – | – | – | – | – | – | – | – | – |
| 8 weeks after treatment | – | – | – | – | – | – | – | – | – |

TABLE 17

Serum ADA test results in 10 mg/kg single dose group

| Sampling time | #1 | #2 | #3 | #4 | #5 | #6 | #7 | #8 | #9 |
|---|---|---|---|---|---|---|---|---|---|
| Before treatment | – | – | – | – | – | – | – | – | – |
| 2 weeks after treatment | – | – | – | – | – | – | – | – | – |
| 4 weeks after treatment | – | – | – | – | – | – | – | – | – |
| 8 weeks after treatment | – | – | – | – | – | – | – | – | – |

(2) Multiple dose treatment:

Study methods: 9 subjects of rheumatoid arthritis were treated with planned therapeutic dose (3 mg/kg) of phase II clinical trial, intravenous infusion at week 0, 2, 6, 10, 14, infusion time was 2 hours, clinical monitoring before each treatment or week 2, 12 after the last treatment. To detect anti-CMAB008 antibody (ADA) in the sera of the subjects repeatedly treated with CMAB008 antibody, blood was collected and serum anti-CMAB008 antibody (ADA) test was performed before each infusion and at week 1, 2, 4, 6, 8, 12 after the last infusion. The detailed ADA test procedures, screening criteria and antibody detection procedures were the same as those of the single dose group.

The results showed that only 1 subject J was test positive in serum anti-CMAB008 antibody test before the third, fourth, and fifth infusion and week 1, 2, 4 after the fifth infusion, detailed results are shown in table 18. Further tests confirmed no neutralizing antibodies, results are shown in table 19.

TABLE 18

Serum ADA test results of multiple doses group

| Sampling time | A | C | D | E | F | G | H | I | J | K |
|---|---|---|---|---|---|---|---|---|---|---|
| Before the 1st treatment | – | – | – | – | – | – | – | – | – | – |
| Before the 2nd treatment | – | – | – | – | – | – | – | – | – | – |
| Before the 3rd treatment | – | – | – | – | – | – | – | – | + | – |
| Before the 4th treatment | – | – | – | – | – | – | – | – | + | – |
| Before the 5th treatment | – | – | – | – | – | – | – | – | + | – |
| 1 week after the 5th treatment | – | – | – | – | – | – | – | ND | + | – |
| 2 weeks after the 5th treatment | – | – | – | – | – | – | – | – | + | – |
| 4 weeks after the 5th treatment | – | – | – | – | – | – | – | – | + | – |
| 6 weeks after the 5th treatment | – | – | – | – | – | – | – | – | – | – |
| 8 weeks after the 5th treatment | – | – | – | – | – | – | – | – | – | – |
| 12 weeks after the 5th treatment | – | – | – | – | – | – | – | – | – | – |

TABLE 19 multiple doses of serum neutralizing antibodies

| Sampling time | J |
|---|---|
| Before treatment | — |
| Before the 3rd treatment | — |
| Before the 4th treatment | — |
| Before the 5th treatment | — |
| 1 week after the 5th treatment | — |
| 2 weeks after the 5th treatment | — |
| 4 weeks after the 5th treatment | — |

Analysis of the serum CMAB008 concentrations in the plasma of subject J found no significant difference in serum drug concentration between this and other subjects.

(3) Phase III clinical studies:

Methods: A randomized, double-blind, parallel, multicenter trial. Before enrollment, patients received at least three months MTX treatment, and a stable dose of MTX in 7.5~20 mg/week, and the disease has not been in satisfactory control. Subjects were treated at 0, 2, 6, 14 weeks with 3 mg/kg of infliximab or placebo by intravenous infusion, simultaneously taking the same dose of MTX weekly. Subjects were follow-uped at week 0, 2, 6, 14, 18 during the study. Efficacy and adverse reactions were evaluated.

Subjects eligible for immunogenicity analysis totaled 339 (Subject should be in the study groups, and must have serum samples collected before treatment and at least one sample after treatment, i.e. serum samples before treatment (T1) must be collected, and at least one serum samples after administration, T2 or T3, should be collected). Detailed ADA test procedures and screening criteria are the same as those of single dose treatment. It was determined that a total of 8 subjects produced anti-CMAB008 antibody after treatment, results are shown in table 20, with antibody production rate of 2.36%; While the anti-Remicade antibody production rate is 16% (J Turon et. Al., Su2013 Clinical Outcome of Pediatric IBD Patients After Measurement of Infliximab Drug and Anti-Drug Antibody Levels. Gastroenterology. 144:5, May 2013, S-531) ADA neutralizing antibody was present in the sera of all ADA-positive subjects, the results are shown in table 21.

TABLE 20

Serum ADA test results in Phase III clinical trial

| Test number | Center # | Drug Number | T1 | T2 | T3 |
|---|---|---|---|---|---|
| 1 | 01 | 1 | – | – | – |
| 2 | | 2 | – | – | – |
| 3 | | 3 | – | – | – |
| 4 | | 4 | – | – | – |
| 5 | | 6 | – | – | – |
| 6 | | 7 | – | – | – |
| 7 | | 8 | – | – | – |
| 8 | | 9 | – | – | – |
| 9 | 04 | 31 | – | – | – |
| 10 | | 32 | – | – | – |
| 11 | | 33 | – | – | – |
| 12 | | 35 | – | – | – |
| 13 | | 37 | – | – | – |
| 14 | | 38 | – | – | – |
| 15 | | 39 | – | – | – |
| 16 | | 40 | – | – | – |
| 17 | | 211 | – | + | + |
| 18 | | 212 | – | – | – |
| 19 | | 214 | – | – | ND |
| 20 | | 215 | – | – | ND |
| 21 | | 216 | – | – | – |
| 22 | | 217 | – | – | ND |
| 23 | | 218 | – | – | – |
| 24 | | 219 | – | – | – |
| 25 | | 371 | – | – | ND |
| 26 | | 372 | – | – | – |
| 27 | | 373 | – | ND | – |
| 28 | | 374 | – | – | ND |
| 29 | | 376 | – | – | – |
| 30 | | 378 | – | – | – |
| 31 | | 379 | – | – | – |
| 32 | | 380 | – | – | – |
| 33 | | 381 | – | – | – |
| 34 | | 385 | – | – | ND |
| 35 | | 386 | – | – | ND |
| 36 | | 387 | – | – | – |
| 37 | | 388 | – | – | ND |
| 38 | 05 | 42 | – | – | – |
| 39 | | 43 | – | – | – |
| 40 | | 44 | – | – | – |

TABLE 20-continued

Serum ADA test results in Phase III clinical trial

| Test number | Center # | Drug Number | T1 | T2 | T3 |
|---|---|---|---|---|---|
| 41 | | 45 | – | – | – |
| 42 | | 46 | – | – | – |
| 43 | | 47 | – | – | – |
| 44 | | 49 | – | ND | – |
| 45 | | 50 | – | – | – |
| 46 | | 292 | – | – | – |
| 47 | | 293 | – | – | – |
| 48 | | 294 | – | – | – |
| 49 | | 295 | – | – | – |
| 50 | | 296 | – | – | – |
| 51 | | 297 | – | – | – |
| 52 | | 298 | – | – | – |
| 53 | 06 | 205 | – | ND | – |
| 54 | | 58 | – | ND | – |
| 55 | | 60 | – | ND | – |
| 56 | | 272 | – | – | – |
| 57 | | 273 | – | – | – |
| 58 | | 274 | – | – | ND |
| 59 | | 275 | – | – | – |
| 60 | | 276 | – | ND | – |
| 61 | | 278 | – | – | – |
| 62 | | 279 | – | – | ND |
| 63 | | 280 | – | – | – |
| 64 | | 402 | – | – | – |
| 65 | | 403 | – | ND | – |
| 66 | | 404 | – | ND | ND |
| 67 | | 405 | – | – | – |
| 68 | | 406 | – | – | – |
| 69 | | 482 | – | – | – |
| 70 | | 483 | – | – | – |
| 71 | | 485 | – | – | – |
| 72 | | 487 | – | – | – |
| 73 | | 488 | – | – | – |
| 74 | | 489 | – | – | – |
| 75 | | 490 | – | – | – |
| 76 | 07 | 61 | – | – | ND |
| 77 | | 62 | – | – | – |
| 78 | | 64 | – | – | – |
| 79 | 07 | 65 | – | – | – |
| 80 | | 66 | – | – | ND |
| 81 | | 67 | – | – | – |
| 82 | | 69 | – | – | – |
| 83 | | 70 | – | – | – |
| 84 | | 285 | – | – | – |
| 85 | | 287 | – | – | – |
| 86 | | 288 | – | – | – |
| 87 | | 289 | – | – | – |
| 88 | 08 | 71 | – | – | – |
| 89 | | 73 | – | – | – |
| 90 | | 74 | – | – | – |
| 91 | | 75 | – | – | ND |
| 92 | | 76 | – | – | – |
| 93 | | 78 | – | – | – |
| 94 | | 79 | – | ND | – |
| 95 | | 491 | – | – | – |
| 96 | | 492 | – | – | – |
| 97 | | 494 | – | – | ND |
| 98 | | 495 | – | – | – |
| 99 | | 496 | – | – | – |
| 100 | | 498 | – | ND | – |
| 101 | | 499 | – | – | – |
| 102 | | 500 | – | – | ND |
| 103 | 09 | 81 | – | – | – |
| 104 | | 82 | – | – | – |
| 105 | | 83 | – | – | – |
| 106 | | 85 | – | + | + |
| 107 | | 86 | – | – | – |
| 108 | | 88 | – | – | – |
| 109 | | 89 | – | – | – |
| 110 | | 332 | – | – | – |
| 111 | | 333 | – | – | – |
| 112 | | 334 | – | – | ND |
| 113 | | 335 | – | – | – |
| 114 | | 336 | – | – | – |
| 115 | | 337 | – | – | ND |

TABLE 20-continued

Serum ADA test results in Phase III clinical trial

| Test number | Center # | Drug Number | T1 | T2 | T3 |
|---|---|---|---|---|---|
| 116 |  | 338 | − | − | − |
| 117 |  | 339 | − | − | − |
| 118 | 09 | 411 | − | − | ND |
| 119 |  | 413 | − | − | − |
| 120 |  | 414 | − | − | ND |
| 121 |  | 415 | − | − | ND |
| 122 |  | 417 | − | − | − |
| 123 |  | 419 | − | − | − |
| 124 |  | 420 | − | − | ND |
| 125 |  | 421 | − | − | − |
| 126 |  | 422 | − | − | ND |
| 127 |  | 424 | − | − | − |
| 128 |  | 425 | − | ND | − |
| 129 |  | 427 | − | − | − |
| 130 |  | 428 | − | − | − |
| 131 |  | 429 | − | + | + |
| 132 |  | 430 | − | − | − |
| 133 |  | 522 | − | ND | − |
| 134 |  | 523 | − | − | − |
| 135 |  | 524 | − | − | − |
| 136 |  | 525 | − | − | ND |
| 137 |  | 526 | − | − | − |
| 138 |  | 528 | − | − | − |
| 139 |  | 529 | − | − | − |
| 140 |  | 530 | − | − | − |
| 141 | 10 | 92 | − | ND | − |
| 142 |  | 93 | − | − | − |
| 143 |  | 96 | − | − | − |
| 144 |  | 97 | − | − | ND |
| 145 |  | 98 | − | − | − |
| 146 |  | 100 | − | − | − |
| 147 | 11 | 501 | − | − | − |
| 148 |  | 502 | − | − | − |
| 149 |  | 503 | − | − | − |
| 150 |  | 504 | − | − | − |
| 151 |  | 505 | − | − | − |
| 152 |  | 506 | − | ND | − |
| 153 |  | 507 | − | − | − |
| 154 |  | 508 | − | − | − |
| 155 |  | 509 | − | − | − |
| 156 |  | 510 | − | − | − |
| 157 | 11 | 511 | − | − | − |
| 158 |  | 512 | − | − | − |
| 159 |  | 513 | − | − | − |
| 160 |  | 514 | − | − | − |
| 161 |  | 515 | − | − | − |
| 162 |  | 516 | − | − | − |
| 163 |  | 517 | − | − | − |
| 164 |  | 518 | − | − | − |
| 165 |  | 519 | − | − | ND |
| 166 |  | 520 | − | − | − |
| 167 |  | 451 | − | − | − |
| 168 |  | 452 | − | − | − |
| 169 |  | 453 | − | − | − |
| 170 |  | 454 | − | − | ND |
| 171 |  | 455 | − | − | − |
| 172 |  | 456 | − | − | ND |
| 173 |  | 458 | − | − | − |
| 174 |  | 459 | − | − | − |
| 175 |  | 460 | − | − | − |
| 176 |  | 461 | − | − | − |
| 177 |  | 462 | − | − | − |
| 178 |  | 463 | − | − | − |
| 179 |  | 464 | − | − | ND |
| 180 |  | 465 | − | − | − |
| 181 |  | 466 | − | − | ND |
| 182 |  | 467 | − | − | − |
| 183 |  | 468 | − | − | ND |
| 184 |  | 469 | − | − | − |
| 185 |  | 470 | − | − | − |
| 186 |  | 101 | − | − | − |
| 187 |  | 102 | − | − | − |
| 188 |  | 103 | − | − | − |
| 189 |  | 104 | − | − | − |
| 190 |  | 105 | − | − | − |
| 191 |  | 106 | − | − | − |
| 192 |  | 107 | − | − | − |
| 193 |  | 108 | − | − | − |
| 194 |  | 109 | − | − | − |
| 195 |  | 110 | − | − | − |
| 196 | 11 | 261 | − | − | − |
| 197 |  | 262 | − | − | − |
| 198 |  | 263 | − | − | − |
| 199 |  | 264 | − | − | − |
| 200 |  | 265 | − | − | − |
| 201 |  | 266 | − | − | ND |
| 202 |  | 267 | − | − | − |
| 203 |  | 268 | − | − | ND |
| 204 |  | 269 | − | − | ND |
| 205 |  | 270 | − | − | − |
| 206 |  | 261 | − | − | − |
| 207 |  | 262 | − | − | − |
| 208 |  | 263 | − | − | − |
| 209 |  | 264 | − | − | − |
| 210 |  | 265 | − | − | − |
| 211 |  | 266 | − | − | ND |
| 212 |  | 267 | − | − | − |
| 213 |  | 268 | − | − | ND |
| 214 |  | 269 | − | − | ND |
| 215 |  | 270 | − | − | − |
| 216 | 12 | 111 | − | − | − |
| 217 |  | 112 | − | − | − |
| 218 |  | 113 | − | + | + |
| 219 |  | 114 | − | − | − |
| 220 |  | 117 | − | − | − |
| 221 |  | 118 | − | + | + |
| 222 |  | 119 | − | − | − |
| 223 |  | 120 | − | − | − |
| 224 |  | 181 | − | + | + |
| 225 |  | 183 | − | − | ND |
| 226 |  | 184 | − | − | − |
| 227 |  | 185 | − | − | − |
| 228 |  | 187 | − | − | − |
| 229 |  | 188 | − | − | ND |
| 230 |  | 189 | − | − | − |
| 231 |  | 191 | − | − | − |
| 232 |  | 192 | − | − | − |
| 233 |  | 193 | − | − | − |
| 234 |  | 195 | − | − | − |
| 235 | 12 | 196 | − | − | − |
| 236 |  | 197 | − | ND | − |
| 237 |  | 198 | − | − | − |
| 238 |  | 200 | − | − | − |
| 239 |  | 231 | − | − | − |
| 249 |  | 233 | − | − | − |
| 241 |  | 234 | − | − | − |
| 242 |  | 236 | − | − | − |
| 243 |  | 237 | − | − | ND |
| 244 |  | 239 | − | − | − |
| 245 |  | 240 | − | − | − |
| 246 |  | 241 | − | − | ND |
| 247 |  | 242 | − | − | − |
| 248 |  | 244 | − | − | − |
| 249 |  | 245 | − | − | − |
| 250 |  | 247 | − | + | + |
| 251 |  | 248 | − | ND | − |
| 252 |  | 249 | − | − | − |
| 253 |  | 251 | − | ND | − |
| 254 |  | 252 | − | − | − |
| 255 |  | 253 | − | − | − |
| 256 |  | 254 | − | − | − |
| 257 |  | 256 | − | − | − |
| 258 |  | 258 | − | − | − |
| 259 |  | 259 | − | − | − |
| 260 |  | 260 | − | − | − |
| 261 |  | 301 | − | − | − |
| 262 |  | 303 | − | − | − |
| 263 |  | 304 | − | − | − |
| 264 |  | 306 | − | − | − |
| 265 |  | 308 | − | − | − |

TABLE 20-continued

Serum ADA test results in Phase III clinical trial

| Test number | Center # | Drug Number | T1 | T2 | T3 |
|---|---|---|---|---|---|
| 266 | | 310 | − | − | − |
| 267 | | 311 | − | − | − |
| 268 | | 312 | − | − | − |
| 269 | | 313 | − | − | − |
| 270 | | 314 | − | − | − |
| 271 | | 316 | − | + | + |
| 272 | | 318 | − | − | − |
| 273 | | 319 | − | − | − |
| 274 | 12 | 320 | − | − | − |
| 275 | | 321 | − | − | − |
| 276 | | 322 | − | ND | − |
| 277 | | 324 | − | − | − |
| 278 | | 325 | − | − | − |
| 279 | | 327 | − | − | − |
| 280 | | 328 | − | − | − |
| 281 | | 329 | − | − | − |
| 282 | | 330 | − | − | − |
| 283 | 13 | 121 | − | ND | − |
| 284 | | 122 | − | − | − |
| 285 | | 124 | − | − | − |
| 286 | | 125 | − | − | − |
| 287 | | 128 | − | − | − |
| 288 | | 130 | − | − | − |
| 289 | | 397 | − | − | ND |
| 290 | | 399 | − | − | ND |
| 291 | 14 | 131 | − | − | − |
| 292 | | 133 | − | − | − |
| 293 | | 135 | − | ND | − |
| 294 | | 136 | − | − | − |
| 295 | | 138 | − | − | − |
| 296 | | 140 | − | − | − |
| 297 | | 471 | − | − | − |
| 298 | | 473 | − | − | − |
| 299 | | 475 | − | − | − |
| 300 | | 477 | − | − | − |
| 301 | | 478 | − | − | − |
| 302 | | 479 | − | − | − |
| 303 | | 480 | − | − | ND |
| 304 | 16 | 151 | − | ND | − |
| 305 | | 153 | − | − | − |
| 306 | | 154 | − | − | − |
| 307 | | 155 | − | − | − |
| 308 | | 156 | − | − | − |
| 309 | | 158 | − | − | − |
| 310 | | 159 | − | − | − |
| 311 | | 160 | − | − | − |
| 312 | | 543 | − | − | − |
| 313 | 16 | 544 | − | − | − |
| 314 | | 545 | − | − | − |
| 315 | | 546 | − | − | − |
| 316 | | 547 | − | − | − |
| 317 | | 548 | − | − | − |
| 318 | | 550 | − | − | − |
| 319 | 17 | 161 | − | − | − |
| 320 | | 162 | − | − | − |
| 321 | | 164 | − | − | − |
| 322 | | 165 | − | − | − |
| 323 | | 167 | − | − | ND |
| 324 | | 168 | − | − | ND |
| 325 | | 169 | − | − | − |
| 326 | | 170 | ND | − | − |
| 327 | | 441 | − | ND | ND |
| 328 | | 443 | − | − | − |
| 329 | | 444 | − | − | ND |
| 330 | | 445 | − | − | − |
| 331 | | 446 | − | − | ND |
| 332 | | 447 | − | − | − |
| 333 | | 448 | − | − | − |
| 334 | | 532 | − | − | − |
| 335 | | 533 | − | − | − |
| 336 | | 534 | − | − | − |
| 337 | | 536 | − | − | − |
| 338 | | 538 | − | − | − |
| 339 | | 539 | − | − | − |

Invalid subjects are not included in the table above, ND indicates sample missed.

Serum neutralizing antibody test (TNF-α toxicity inhibition blocking test in L929 cell):

Detailed experimental methods and screening criteria are the same as those of single dose treatment group.

The results are shown in the following table, neutralizing antibodies are present in the serum of all ADA-positive subjects.

TABLE 21

Serum neutralizing antibody test in phase III clinical trial

| Test | Center # | Drug | T1 | T2 | T3 |
|---|---|---|---|---|---|
| 17 | 04 | 211 | ND | + | + |
| 106 | 09 | 85 | ND | + | + |
| 131 | | 429 | ND | + | + |
| 218 | 12 | 113 | ND | + | + |
| 221 | | 118 | ND | + | + |
| 224 | | 181 | ND | + | + |
| 250 | | 247 | ND | + | + |
| 271 | | 316 | ND | + | + |

As shown in table 20, table 21, valid subjects totaled 339 (Subjects should be in the study groups, and must have serum samples collected before treatment and at least one sample after treatment, i.e. serum samples before treatment (T1) must be collected, and at least one serum samples after treatment, T2 or T3, should be collected). It was determined that a total of 8 subjects produced anti-CMAB008 antibody after treatment, with antibody production rate of 2.36%. While the Remicade anti-antibody production rate is 16% (J Turon et. Al., Su2013 Clinical Outcome of Pediatric IBD Patients After Measurement of Infliximab Drug and Anti-Drug Antibody Levels. Gastroenterology. 144:5, May 2013, S-531), the ADA production rate for CMAB008 was significantly lower than that of Remicade.

The invention claimed is:

1. A method of producing a recombinant chimeric anti-TNF-α monoclonal antibody, wherein said method comprises:
   a) transfecting a host cell with a polynucleotide encoding a recombinant chimeric anti-TNF-α monoclonal antibody, the polynucleotide comprising a light chain nucleic acid sequence of SEQ ID NO: 1 and a heavy chain nucleic acid sequence of SEQ ID NO: 3; wherein the host cell is a Chinese hamster ovarian cell lacking the GS gene (CHO-CR-GS$^{-/-}$);
   b) screening clones expressing the chimeric anti-TNF-α monoclonal antibody; and
   c) culturing the host cell in serum-free conditions to produce the recombinant chimeric anti-TNF-α monoclonal antibody,
      wherein the host cell is cultured in a pH of 6.5 to 6.7, in a temperature of 34° C. to 37° C. and in an osmotic pressure of 345 mOsm/kg to 360 mOsm/kg,
      wherein the chimeric anti-TNF-α monoclonal antibody does not comprise Gal-α1,3-Gal terminal galactose connection or a NGNA terminal sialic acid modification.

2. The method of producing a recombinant chimeric anti-TNF-α monoclonal antibody according to claim 1, wherein the nucleic acid sequences for the light chain and heavy chain of the recombinant chimeric anti-TNF-α monoclonal antibody are designed and synthesized according to the codons mostly preferred by Chinese hamster.

3. The method of claim 1, wherein the host cell is cultured in a pH of 6.7.

4. The method of claim 1, wherein the host cell is cultured in a temperature of 35° C.

5. The method of claim 1, wherein the host cell is cultured in an osmotic pressure of 345 mOsm/kg.

6. A method of producing a recombinant chimeric anti-TNF-α monoclonal antibody, wherein said method comprises:
   a) transfecting a host cell with a polynucleotide encoding a recombinant chimeric anti-TNF-α monoclonal antibody, the polynucleotide comprising a light chain nucleic acid sequence of SEQ ID NO: 1 and a heavy chain nucleic acid sequence of SEQ ID NO: 3 wherein the host cell is a Chinese hamster ovarian cell lacking the GS gene (CHO-CR-GS$^{-/-}$);
   b) screening clones expressing the chimeric anti-TNF-α monoclonal antibody; and
   c) culturing the host cell in serum-free conditions to produce the recombinant chimeric anti-TNF-α monoclonal antibody, isolating and purifying antibody, wherein the pH for cell culture is: 6.5~7.0, wherein the chimeric anti-TNF-α monoclonal antibody does not comprise Gal-α1,3-Gal terminal galactose connection or a NGNA terminal sialic acid modification.

7. The method of claim 6, wherein the pH for cell culture is 6.7.

8. A method of producing a recombinant chimeric anti-TNF-α monoclonal antibody, wherein said method comprising:
   a) transfecting a host cell with a polynucleotide encoding a recombinant chimeric anti-TNF-α monoclonal antibody, the polynucleotide comprising a light chain nucleic acid sequence of SEQ ID NO: 1 and a heavy chain nucleic acid sequence of SEQ ID NO: 3, wherein the host cell is a Chinese hamster ovarian cell lacking the GS gene (CHO-CR-GS$^{-/-}$);
   b) screening clones expressing the chimeric anti-TNF-α monoclonal antibody; and
   c) culturing the host cell in serum-free conditions to produce the recombinant chimeric anti-TNF-α monoclonal antibody, wherein the temperature for cell culture is: 34° C.~37° C., wherein the chimeric anti-TNF-α monoclonal antibody does not comprise Gal-α1,3-Gal terminal galactose connection or a NGNA terminal sialic acid modification.

9. The method of claim 8, wherein the cell culture temperature is 35° C.

10. A method of producing a recombinant chimeric anti-TNF-α monoclonal antibody, wherein said method comprises:
    a) transfecting a host cell with a polynucleotide encoding a anti-TNF-α monoclonal antibody, the polynucleotide comprising a light chain nucleic acid sequence of SEQ ID NO: 1 and a heavy chain nucleic acid sequence of SEQ ID NO: 3, wherein the host cell is a Chinese hamster ovarian cell lacking the GS gene (CHO-CR-GS$^{-/-}$);
    b) screening clones expressing the chimeric anti-TNF-α monoclonal antibody; and
    c) culturing the host cell in serum-free conditions to produce the recombinant chimeric anti-TNF-α monoclonal antibody, wherein the osmotic pressure of cell culture is: 295 mOsm/kg 360 mOsm/kg, wherein the chimeric anti-TNF-α monoclonal antibody does not comprise Gal-α1,3-Gal terminal galactose connection or a NGNA terminal sialic acid modification.

11. The method of claim 10, wherein the osmotic pressure of cell culture is 345 mOsm/kg.

12. A method of producing a recombinant anti-TNF-α chimeric monoclonal antibody, said method comprising:
    a) transfecting a host cell with a polynucleotide encoding a recombinant chimeric anti-TNF-α monoclonal antibody, the polynucleotide comprising a light chain nucleic acid sequence of SEQ ID NO: 1 and a heavy chain nucleic acid sequence of SEQ ID NO: 3, wherein the host cell is a Chinese hamster ovarian cell lacking the GS gene (CHO-CR-GS$^{-/-}$);
    b) screening clones expressing the chimeric anti-TNF-α monoclonal antibody; and
    c) culturing the host cell in serum-free conditions to produce the recombinant chimeric anti-TNF-α monoclonal antibody wherein pH for cell culture is: 6.5~7.0; the temperature for cell culture is: 34° C.~37° C.; the osmotic pressure of cell culture is: 295 mOsm/kg 360 mOsm/kg, wherein the chimeric anti-TNF-α monoclonal antibody does not comprise Gal-α1,3-Gal terminal galactose connection or a NGNA terminal sialic acid modification.

13. The method of claim 12, wherein pH for cell culture is 6.7.

14. The method of claim 12, wherein the temperature for cell culture is 35° C.

15. The method of claim 12, wherein the osmotic pressure of cell culture is 345 mOsm/kg.

* * * * *

SEQUENCE LISTING

<160> NUMBER OF SEQ ID NOS: 4

<210> SEQ ID NO 1
<211> LENGTH: 642
<212> TYPE: DNA
<213> ORGANISM: Artificial Sequence
<220> FEATURE:
<223> OTHER INFORMATION: synthetic

```
<220> FEATURE:
<221> NAME/KEY: misc_feature
<222> LOCATION: (1)..(642)
<223> OTHER INFORMATION: nucleotide sequence of a light chain

<400> SEQUENCE: 1
gacatcctgc tgacccagtc tcccgccatc ctgtctgtgt ctcccggcga gagagtgtct    60
ttctcttgca gagcctctca gttcgtgggc tcttctatcc actggtacca gcagagaacc   120
aacggctctc ccagactgct gatcaagtac gcctctgagt ctatgtctgg catcccctct   180
agattctctg gctctggctc tggcaccgac ttcaccctgt ctatcaacac cgtggagtct   240
gaggacatcg ccgactacta ctgccagcag tctcactctt ggcccttcac cttcggctct   300
ggcaccaacc tggaggtgaa gagaaccgtg gccgccccct ctgtgttcat cttccccccc   360
tctgacgagc agctgaagtc tggcaccgcc tctgtggtgt gcctgctgaa caacttctac   420
cccagagagg ccaaggtgca gtggaaggtg acaacgccc tgcagtctgg caactctcag   480
gagtctgtga ccgagcagga ctctaaggac tctacctact ctctgtcttc taccctgacc   540
ctgtctaagg ccgactacga aagcacaag gtgtacgcct gcgaggtgac ccaccagggc   600
ctgtcttctc ccgtgaccaa gtctttcaac agaggcgagt gc                      642

<210> SEQ ID NO 2
<211> LENGTH: 214
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(214)
<223> OTHER INFORMATION: amino acid sequence of a light chain

<400> SEQUENCE: 2

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 1350
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1350)
<223> OTHER INFORMATION: nucleotide sequence of a heavy chain

<400> SEQUENCE: 3

| | | | | | |
|---|---|---|---|---|---|
| gaggtgaagc | tggaggagtc | tggcggcggc | ctggtgcagc | ccggcggctc | tatgaagctg | 60 |
| tcttgcgtgg | cctctggctt | catcttctct | aaccactgga | tgaactgggt | gagacagtct | 120 |
| cccgagaagg | gcctggagtg | ggtggccgag | atcagatcta | agtctatcaa | ctctgccacc | 180 |
| cactacgccg | agtctgtgaa | gggcagattc | accatctcta | gagacgactc | taagtctgcc | 240 |
| gtgtacctgc | agatgaccga | cctgagaacc | gaggacaccg | gcgtgtacta | ctgctctaga | 300 |
| aactactacg | gctctaccta | cgactactgg | ggccagggca | ccaccctgac | cgtgtcttct | 360 |
| gcctctacca | agggccccte | tgtgttcccc | ctggcccect | cttctaagtc | tacctctggc | 420 |
| ggcaccgccg | ccctgggctg | cctggtgaag | gactacttcc | ccgagcccgt | gaccgtgtct | 480 |
| tggaactctg | gcgccctgac | ctctggcgtg | cacaccttcc | ccgccgtgct | gcagtcttct | 540 |
| ggcctgtact | ctctgtcttc | tgtggtgacc | gtgccctctt | cttctctggg | cacccagacc | 600 |
| tacatctgca | acgtgaacca | caagccctct | aacaccaagg | tggacaagaa | ggtggagccc | 660 |
| aagtcttgcg | acaagaccca | cacctgcccc | cctgccccg | ccccgagct | gctgggcggc | 720 |
| ccctctgtgt | tcctgttccc | ccccaagccc | aaggacaccc | tgatgatctc | tagaaccccc | 780 |
| gaggtgacct | gcgtggtggt | ggacgtgtct | cacgaggacc | ccgaggtgaa | gttcaactgg | 840 |
| tacgtggacg | gcgtggaggt | gcacaacgcc | aagaccaagc | ccagagagga | gcagtacaac | 900 |
| tctacctaca | gagtggtgtc | tgtgctgacc | gtgctgcacc | aggactggct | gaacggcaag | 960 |
| gagtacaagt | gcaaggtgtc | taacaaggcc | ctgcccgccc | ccatcgagaa | gaccatctct | 1020 |
| aaggccaagg | gccagcccag | agagcccag | gtgtacaccc | tgccccctc | tagagacgag | 1080 |
| ctgaccaaga | accaggtgtc | tctgacctgc | ctggtgaagg | gcttctaccc | ctctgacatc | 1140 |
| gccgtggagt | gggagtctaa | cggccagccc | gagaacaact | acaagaccac | ccccccgtg | 1200 |
| ctggactctg | acggctcttt | cttcctgtac | tctaagctga | ccgtggacaa | gtctagatgg | 1260 |
| cagcagggca | acgtgttctc | ttgctctgtg | atgcacgagg | ccctgcacaa | ccactacacc | 1320 |
| cagaagtctc | tgtctctgtc | tcccggcaag | | | | 1350 |

<210> SEQ ID NO 4
<211> LENGTH: 450
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(450)
<223> OTHER INFORMATION: amino acid sequence of a heavy chain

<400> SEQUENCE: 4

```
Glu Val Lys Leu Glu Glu Ser Gly Gly Gly Leu Val Gln Pro Gly Gly
1               5                   10                  15

Ser Met Lys Leu Ser Cys Val Ala Gly Phe Ile Phe Ser Asn His
        20                  25                  30

Trp Met Asn Trp Val Arg Gln Ser Pro Glu Lys Gly Leu Glu Trp Val
            35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```